(12) United States Patent
Konno

(10) Patent No.: US 11,179,115 B2
(45) Date of Patent: Nov. 23, 2021

(54) X-RAY CT DATA PROCESSING DEVICE AND X-RAY CT DEVICE COMPRISING SAME

(71) Applicant: Hitachi, Ltd., Tokyo (JP)

(72) Inventor: Yasutaka Konno, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 126 days.

(21) Appl. No.: 15/763,126

(22) PCT Filed: Oct. 18, 2016

(86) PCT No.: PCT/JP2016/080787
§ 371 (c)(1),
(2) Date: Mar. 26, 2018

(87) PCT Pub. No.: WO2017/073399
PCT Pub. Date: May 4, 2017

(65) Prior Publication Data
US 2018/0263576 A1    Sep. 20, 2018

(30) Foreign Application Priority Data
Oct. 27, 2015    (JP) .............................. JP2015-210701

(51) Int. Cl.
*A61B 6/03* (2006.01)
*A61B 6/00* (2006.01)
*G06T 11/00* (2006.01)

(52) U.S. Cl.
CPC ............ *A61B 6/032* (2013.01); *A61B 6/4241* (2013.01); *A61B 6/463* (2013.01); *A61B 6/482* (2013.01);
(Continued)

(58) Field of Classification Search
CPC ....... A61B 6/482; A61B 6/4241; A61B 6/405; G06T 2211/408
See application file for complete search history.

(56) References Cited

U.S. PATENT DOCUMENTS

| | | | |
|---|---|---|---|
| 6,704,725 B1* | 3/2004 | Lee | G06K 9/64 |
| 2013/0315371 A1* | 11/2013 | Simon | A61B 6/505 |
| | | | 378/54 |

(Continued)

FOREIGN PATENT DOCUMENTS

| | | |
|---|---|---|
| CN | 103764037 A | 4/2014 |
| JP | 2014166351 A | 9/2014 |
| JP | 2014239840 A | 12/2014 |

OTHER PUBLICATIONS

International Search Report dated Dec. 27, 2016 for International Patent Application No. PCT/JP2016/080787.
(Continued)

*Primary Examiner* — David P Porta
*Assistant Examiner* — Mamadou Faye
(74) *Attorney, Agent, or Firm* — Baker Botts L.L.P.

(57) ABSTRACT

An X-ray CT data processing device is provided which when multi-energy photography is performed with an energy-separation type detector, and a subject is separated into a plurality of standard materials to create an image, estimates the appropriateness of posited standard materials, and in order to determine appropriate standard materials with satisfactory accuracy, processes CT data respectively acquired in a plurality of detection energy ranges to create a reconstructed image separated into predetermined standard materials. The X-ray CT data processing device is equipped with a standard material data calculating part which calculates energy-independent physical quantities for a plurality of standard materials respectively using different combinations of a plurality of the CT data, and creates a plurality of standard material data for the same standard material, and an appropriateness determination index creating part which creates an index for determining the appropriateness of the (Continued)

standard material, based on the plurality of standard material data calculated by the standard material data calculating part.

11 Claims, 15 Drawing Sheets

(52) U.S. Cl.
CPC .......... *A61B 6/5205* (2013.01); *A61B 6/5217* (2013.01); *G06T 11/003* (2013.01); *G06T 11/005* (2013.01); *G06T 2207/10081* (2013.01); *G06T 2211/408* (2013.01)

(56) References Cited

U.S. PATENT DOCUMENTS

| | | |
|---|---|---|
| 2015/0164456 A1 | 6/2015 | Takamatsu et al. |
| 2016/0187509 A1* | 6/2016 | Boot ..................... G06T 3/4038 382/109 |
| 2017/0228897 A1* | 8/2017 | Holt ..................... G06K 9/6218 |
| 2018/0114314 A1* | 4/2018 | Butler ..................... A61B 6/032 |

OTHER PUBLICATIONS

Office Action, dated Aug. 5, 2020, which issued during the prosecution of Chinese Application No. 201680055695.0, which corresponds to the present application (with English translation).

\* cited by examiner

X-RAY CT DATA PROCESSING DEVICE AND X-RAY CT DEVICE COMPRISING SAME

CROSS-REFERENCE TO RELATED APPLICATIONS

This application is a national phase claiming the benefit of and priority to International Patent Application No. PCT/JP2016/080787, entitled "X-RAY CT DATA PROCESSING DEVICE AND X-RAY CT DEVICE COMPRISING SAME", filed Oct. 18, 2016, which claims priority to Japanese Patent Application No. 2015-210701, filed Oct. 27, 2015, which are hereby incorporated by reference in their entireties.

TECHNICAL FIELD

The present invention relates to a technology of processing data acquired by an X-ray CT device, and particularly to a technology of performing separation into a plurality of standard materials using projected data obtained by photography by an X-ray CT device equipped with an energy separation type X-ray detector of energy-separating incident X-rays into a plurality of energy ranges to measure the same.

BACKGROUND ART

An X-ray CT device is a device which calculates an X-ray absorption coefficient (linear attenuation coefficient) from projected data being X-ray transmitted images of a subject photographed from plural directions and acquires a reconstructed image being a tomographic image of the subject.

Further, there have recently been obtained by a dual energy photography method, many reconstructed images such as a monochromatic X-ray equivalent image, a standard material density image, an effective atomic number image, an electron density image, a photoelectric effect image, a Compton scattered image, an absorption coefficient image at a spectrum other than the above spectrums, etc. Such reconstructed images will subsequently be described as multi-energy images. This photography method is capable of, for example, acquiring images by plural X-rays different in energy spectrum and separating the same into a plurality of standard materials by using their projected data or reconstructed images to obtain images for the respective standard materials.

At this time, it is desirable to perform the separation into the standard materials with satisfactory accuracy. There has therefore been proposed in, for example, Patent Literature 1, a method of creating images in a plurality of energy bands from results obtained by the dual energy photography method and performing separation using images in bands suitable for the respective standard materials to thereby enhance the accuracy of the separation.

CITATION LIST

Patent Literature

PTL 1: Japanese Patent Application Laid-Open No. 2014-239840

SUMMARY OF INVENTION

Technical Problem

The X-ray CT device (hereinafter described as a dual energy CT device) using the above-described dual energy photography method is accompanied by a problem that when a material assumed to be a standard material is different from an actual material although the separation is done assuming the standard material, the material is expressed as the sum of a plurality of standard materials, and the separation is performed such that an actually-nonexistent material exists.

Further, a problem arises in that when the assumed standard material is different from the actual material or the inappropriate standard material is selected, the quantity such as a calculated density, a presence rate or the like is not brought to the correct value and assumes a value degraded in quantitativeness. Further, it is difficult to determine from the result of separation whether the assumed standard material is an appropriate material close to the actual material.

The above-described problems cannot be solved even if a technology of enhancing such a separation accuracy as described in Patent Literature 1, for example is applied thereto. That is, even if an attempt is made to improve the accuracy of separation by using the technology of Patent Literature 1, it is not possible to determine whether the standard material is appropriate. Therefore, even when there is an inappropriate standard material, the separation accuracy cannot be improved. When the standard material is not appropriate, the accuracy of separation into each standard material is degraded. Further, since the appropriate energy band used for separation depends on the standard material, it is not possible to use the appropriate energy band when the standard material is not appropriate.

Solution to Problem

In order to solve the above problems, there is provided an X-ray CT data processing device of the present invention being an X-ray CT data processing device which processes CT data respectively acquired in a plurality of detection energy ranges and separates the CT data into predetermined standard materials to create standard material data. The X-ray CT data processing device is equipped with a standard material data calculating part which calculates energy-independent physical quantities for a plurality of standard materials respectively by using different combinations of a plurality of the CT data and creates a plurality of the standard material data for the same standard material, and an appropriateness determination index creating part which creates an appropriateness determination index being an index for determining the appropriateness of the standard material, based on a plurality of the standard material data calculated by the standard material data calculating part. Here, the CT data means projected data and reconstructed images acquired by the X-ray CT device.

Further, the X-ray CT device of the present invention is equipped with an X-ray generation part which irradiates X-rays, an X-ray detection part which measures the X-rays to obtain CT data, a control part which controls the X-ray generation part or/and the X-ray detection part to obtain the CT data in three or more different detection energy ranges, and an arithmetic part which processes the CT data and separates the CT data into predetermined standard materials to create a reconstructed image.

The arithmetic part is equipped with the above X-ray CT data processing device and a reconstructed image creating part which creates the reconstructed image by using the standard material data obtained in the X-ray CT data processing device.

ADVANTAGEOUS EFFECTS OF INVENTION

According to the present invention, it is possible to determine whether a standard material is appropriate. The standard material can thus be optimized. It is also possible to prevent separation from being made such that an actually-nonexistent material exists. Further, it is possible to improve the quantitation of quantities such as a density, a presence rate, etc. calculated from an image of each standard material, etc.

DESCRIPTION OF EMBODIMENTS

Embodiments of an X-ray CT device and an X-ray CT data processing device according to the present invention will hereinafter be described.

The X-ray CT data processing device is an X-ray CT data processing device which processes CT data respectively acquired in a plurality of detection energy ranges and separates them into predetermined standard materials to create a reconstructed image. The X-ray CT data processing device is equipped with a standard material data calculating part which calculates energy-independent physical quantities for a plurality of standard materials, respectively using different combinations of a plurality of the CT data and creates a plurality of standard material data for the same standard material, and an appropriateness determination index creating part which creates an index for determining the appropriateness of the standard material, based on the plural standard material data calculated by the standard material data calculating part. Here, the CT data means projected data and a reconstructed image obtained in the X-ray CT device.

The X-ray CT device is one in which an arithmetic section processing CT data is equipped with a function of the above-described X-ray CT data processing device. In addition to the arithmetic section, the X-ray CT device is equipped with an X-ray generation section which irradiates X-rays, an X-ray detection section which obtains the CT data obtained by measuring the X-rays, and a control section which controls the X-ray generation section or/and the X-ray detection section to acquire the CT data in three or more different energy ranges.

The configuration and operation of one embodiment of the X-ray CT device to which the present invention is applied will hereinafter be described with reference to the drawings. Although the following embodiments will principally describe an X-ray CT device equipped with X-ray detectors of an energy separation system, particularly, photon counting type X-ray detectors as means of acquiring CT data in a plurality of detection energy ranges, the present invention is not limited to this so long as it can acquire CT data in a plurality of detection energy ranges.

Figure 1:
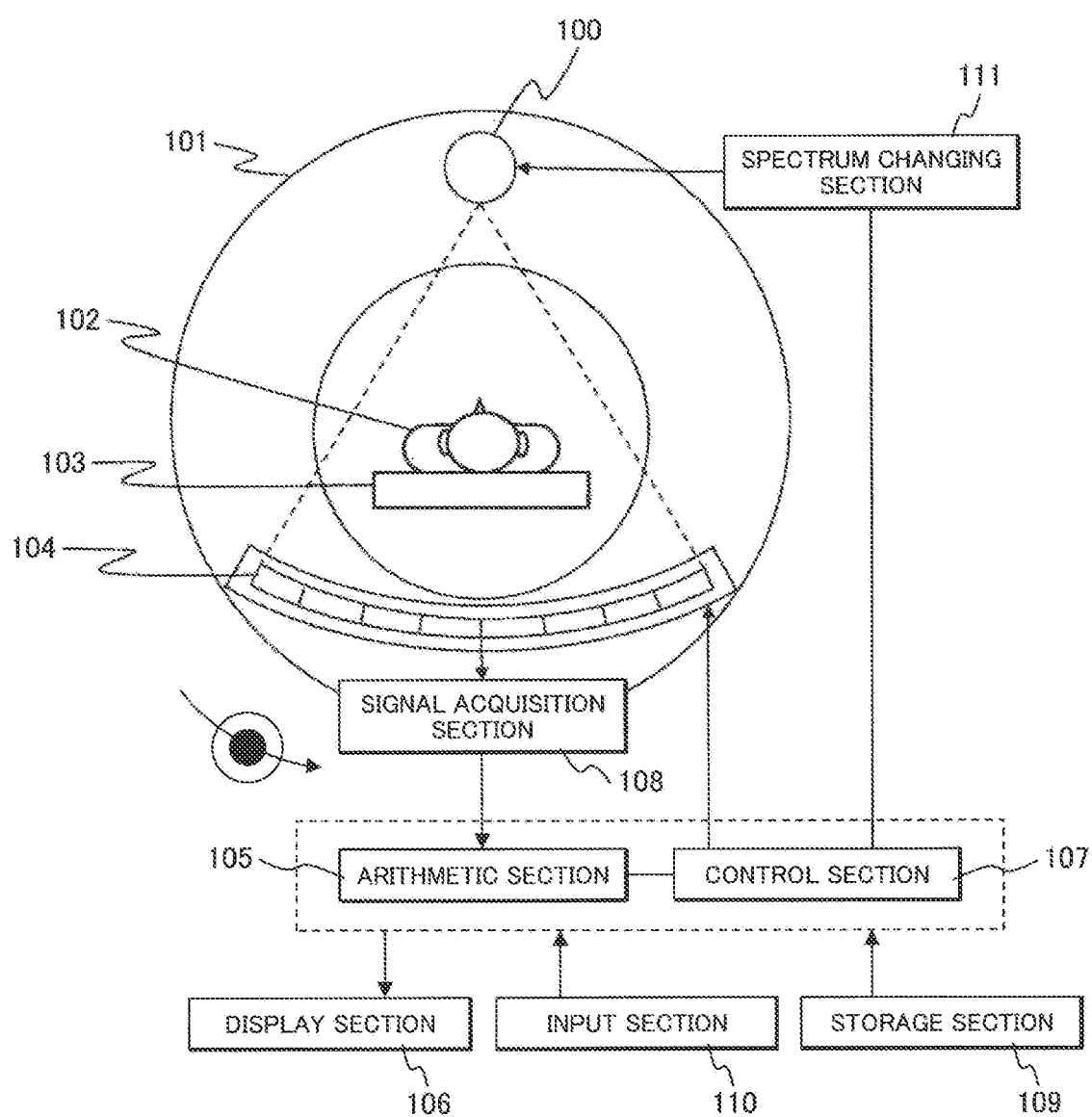
FIG. 1 is a schematic diagram showing an embodiment of an X-ray CT device to which the present invention is applied.

As shown in FIG. 1, the X-ray CT device according to the present embodiment is equipped with, as a photographing system, an X-ray source 100, a spectrum changing section 111, X-ray detectors 104 each disposed in an irradiation range of X-rays irradiated from the X-ray source 100, and a gantry rotating section 101 which causes these X-ray source 100 and X-ray detectors 104 to be disposed opposite to each other, and is rotated centering on a predetermined rotating axis. An opening in which a subject 102 is inserted is provided in the center of the gantry rotating section 101. A bed top plate 103 on which the subject 102 is laid is disposed within the opening. The bed top plate 103 and the gantry rotating section 101 are configured to be movable relatively in a predetermined direction.

The X-ray source 100 in the present embodiment makes an electron beam accelerated by, for example, a tube voltage collide with a target metal such as tungsten, molybdenum or the like and thereby generates X-rays from its collision position (focal point).

The spectrum changing section 111 changes, for example, a tube voltage or an X-ray filter to change a spectrum of each X-ray irradiated from the focal point. As this X-ray filter, there may be mentioned, for example, a metal such as tungsten, molybdenum, copper, tin, aluminum, iron, an alloy of these, etc.

Also, the X-ray CT device is equipped with, as a control system which controls the photographing system of these, and a signal processing system which processes signals acquired by the X-ray detectors 104 accompanying the operation of the photographing system, a control section 107, a signal acquisition section 108, an arithmetic section 105, a display section 106, an input section 110, and a storage section 109, etc.

The control section 107 includes an X-ray control unit which controls the operation of a generation drive source of the X-ray source 100, a reading control unit which controls a signal reading operation of each X-ray detector 104, a photographing control unit which controls the rotation of the gantry rotating section 101 and the movement of the bed top plate 103, and an entire control unit which controls the whole of these respective units.

The control section 107 and the arithmetic section 105 can construct some or all thereof as a system including a CPU (Central Processing Unit), a memory, and the storage section 109. The function of each part configuring the control section 107 and the arithmetic section 105 can be realized by loading a program stored in advance in the storage section 109 into the memory by the CPU and executing the same thereby. Some of the functions can also be configured of hardware such as an ASIC (Application Specific Integrated Circuit) or an FPGA (Field Programmable Gate Array) or the like.

Unless otherwise explained, the elements which configure the photographing system, control system and signal processing system have the same configurations as the elements included in the known X-ray CT device and have similar functions.

The X-ray detectors 104 are arcuately disposed in plural form approximately centering on the X-ray source 100 and rotated accompanying the rotation of the gantry rotating section 101 while maintaining a positional relationship with the X-ray source 100. Incidentally, although the X-ray detectors 104 are shown as eight in number in FIG. 1 for the purpose of simplifying the description, for example, about 40 are used in an actual device. Further, an X-ray grid (not shown) is arranged in front of the X-ray detectors 104. Of X-rays irradiated from the X-ray source 100, X-rays scattered by the subject 102 or the like are prevented from entering each X-ray detector 104.

Figure 2:
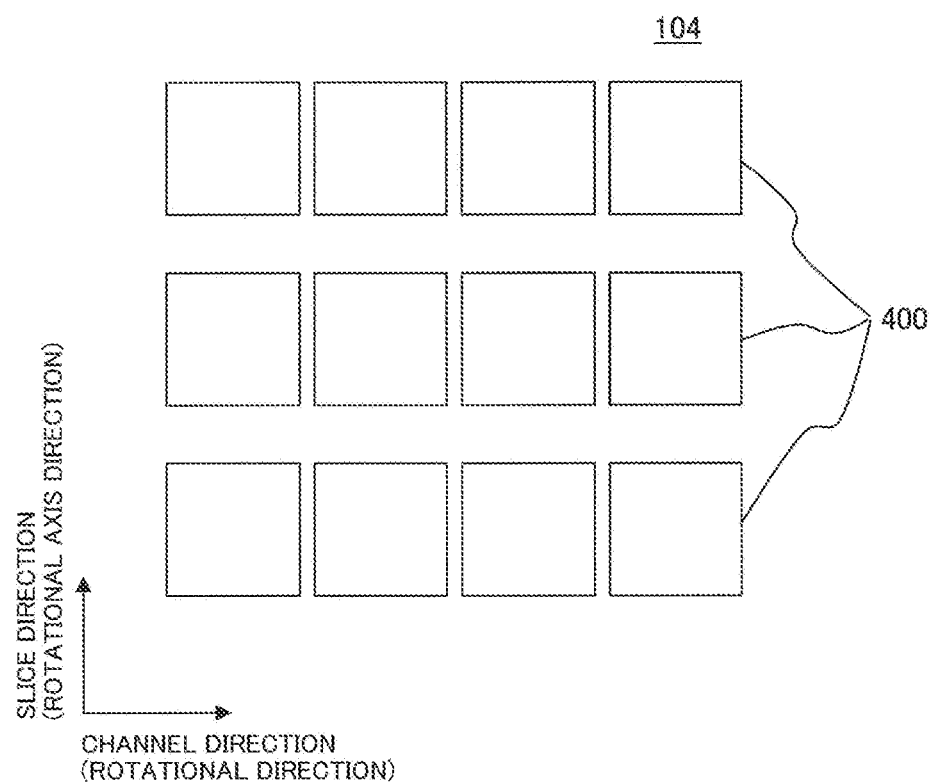
FIG. 2 is a diagram showing an arrangement example of X-ray detecting elements 110 of the X-ray CT device of FIG. 1.

The X-ray detector 104 has, as illustrated in FIG. 2, for example, a structure in which a plurality of photon counting type X-ray detecting elements 400 are two-dimensionally arranged in a channel direction and a slice direction. Here, FIG. 2 shows some of the X-ray detecting elements 400 arranged in the X-ray detector 104 and is one described by cutting out, as the X-ray detecting elements 400, four in the channel direction and three in the slice direction. Further, the X-ray detecting elements 400 are arranged in such a manner that the channel direction and a rotational direction are made coincident with each other, and the slice direction and a rotational axis direction are made coincident with each other.

Figure 3:
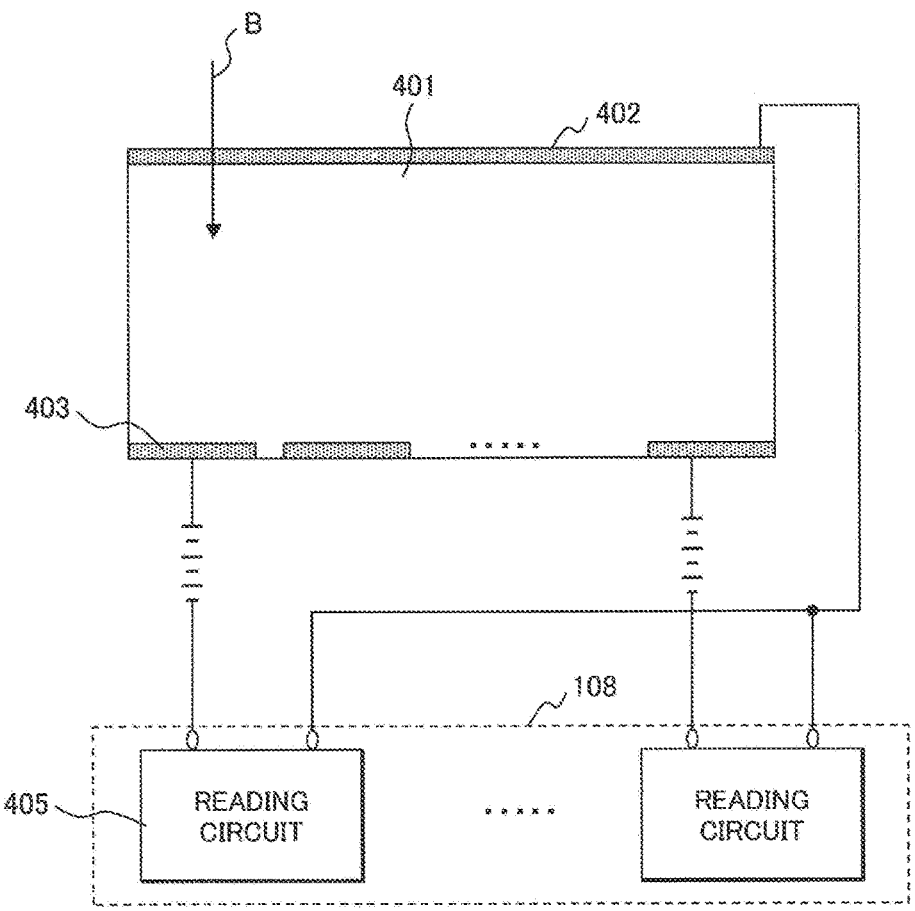
FIG. 3 is an explanatory diagram showing one example of a structure of an X-ray detector 104 of the X-ray CT device of FIG. 1.

As shown in FIG. 3, for example, each X-ray detecting element 400 of the X-ray detector 104 has a structure in which positive and negative electrodes 402 and 403 are provided so as to interpose a detection layer 401 therebetween, and reading circuits 405 of the signal acquisition section 108 are connected to those electrodes. In the present embodiment, the negative electrode 402 is a structure common among the respective X-ray detecting elements 400.

Further, the X-rays enters from the negative electrode 402 side to the detection layer 401 as indicated by an arrow 404. The detection layer 401 is made of a semiconductor material such as CdTe (Cadmium Telluride), CdZnTe (Cadmium Zinc Telluride), Si (Silicon) or the like, and detects the entered X-ray photons and produces an electric charge having a quantity corresponding to its energy. The reading circuit 405 reads out the electric charge generated in the detection layer 401 at predetermined sampling intervals and separates the energy of the entered X-ray photons into a plurality of energy ranges, based on a predetermined threshold value according to an electric signal generated by the electric charge.

For example, the two energy ranges are discriminated depending on an energy range (hereinafter described as a low energy range) being less than the predetermined threshold value and an energy range (hereinafter described as a high energy range) greater than or equal to the predetermined threshold value. Such discrimination is performed for each sampling. When X-ray photons are entered, they are separated into the high energy range and the low energy range, and their numbers of X-ray photons are counted every view.

Figure 4:
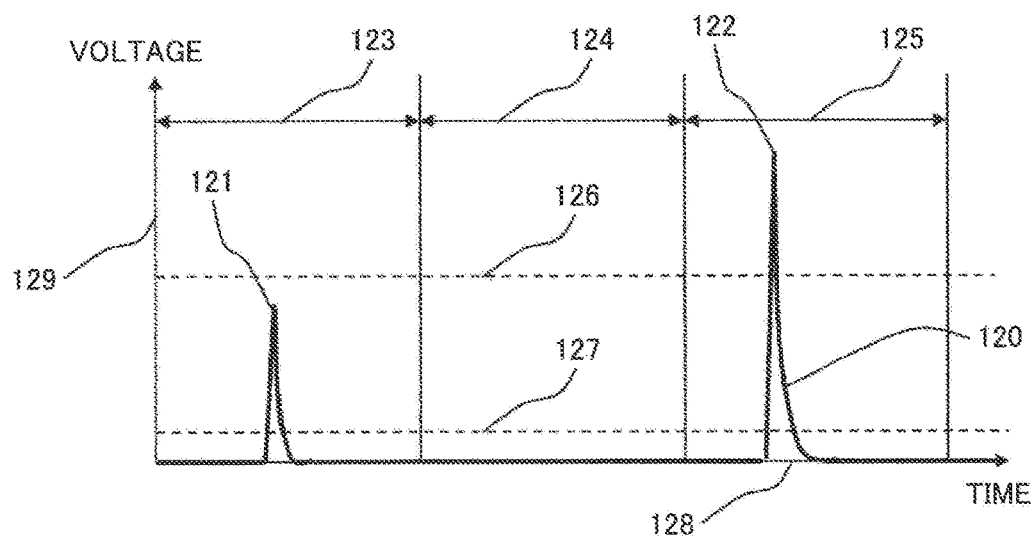
FIG. 4 is an explanatory diagram for describing one example of an energy separating method that the present invention adopts.

One example of a separating method will be described with reference to FIG. 4. FIG. 4 is a graph showing a voltage 120 generated by a generated electric charge. A horizontal axis 128 indicates the time, and a vertical axis 129 indicates the voltage. In the example illustrated in the drawing, an X-ray is made to enter during a sampling time 123 so that a pulse output 121 is generated. An X-ray is made to enter during a sampling time 125 so that a pulse output 122 is generated. Incidentally, although FIG. 4 shows the case where sampling is done not only with timing at which the X-rays are made incident, but also periodically even when the X-rays are not made incident (sampling time 124), sampling may be performed with timing at which X-ray photons are made incident.

The reading circuit (405 in FIG. 3) sorts, for each sampling, the maximum value of an output voltage, an energy threshold value 126, and an energy threshold value 127 during a section for the sampling by comparing them. The energy threshold value 126 is used to separate the entered X-ray photons into the high energy range or the low energy range. The energy threshold value 127 is used to determine whether the X-ray photons are made to be input.

Here, since the output voltage 120 fluctuates due to circuit noise of the X-ray detector 104 even when no X-rays are entered, the energy threshold value 127 is required to have a value larger than zero in order to prevent it from being misdetected as a signal by the X-ray. It is determined by using these energy threshold values that the input of the X-ray photons is absent because the output voltage 120 is not greater than the energy threshold value 127 during the sampling time 124 of FIG. 4, for example.

Further, since the output voltage 120 is larger than the energy threshold value 126 during the sampling time 125, it is determined that an X-ray in the high energy range is made incident. Since the output voltage 120 is larger than the energy threshold value 127 but not greater than the energy threshold value 126 during the sampling time 123, it is determined that an X-ray in the low energy range is made incident. The presence or absence of incidence thereof and the separation of the energy ranges are performed in the above-described manner.

Incidentally, the energy range separating method may use, for example, an integrated value of an output voltage during sampling instead of performing separation by using the maximum value of the output voltage during sampling, and is not limited to the above method.

Also, although the above description has been made about the case where each of the X-ray detectors is the photon counting type which counts the X-ray photons, this is one example but not limited to the present invention. For example, a current measurement type X-ray detector having a plurality of different ranges different in detection energy may be adopted. Such an X-ray detector is, for example, an X-ray detecting element having a structure in which a scintillator is bonded to a photodiode, and has a structure in which a plurality of detection energy ranges are realized by providing each scintillator different in thickness and raw material.

Further, another example has a structure in which a set of a photodiode and a scintillator bonded to each other is laminated in plural form in an X-ray incident direction. At this time, since the scintillator on the X-ray incident side absorbs X-rays and changes an X-ray spectrum, an X-ray spectrum incident to another scintillator detecting the penetrated X-rays is changed, whereby a plurality of detection energy ranges can be realized.

In light of the above configuration, the general photographing operation of the X-ray CT device will be described by taking for example the case where the energy range is two in number and the spectrum of the irradiated X-ray is two in number. This is however intended to simplify the description, but not limited to the present invention. The energy range may be provided three or more, and the spectrum of the irradiated X-ray may be changed to three or more types and used.

First, when a photographer inputs photographing conditions from the input section 110 and inputs the start of actual photographing, the control section 107 controls the irradiation of X-rays from the X-ray source 100 and the gantry rotating section 101 and starts photographing. At this time, assume that, for example, an electron beam is accelerated by a tube voltage of 140 kV and an X-ray is irradiated from the X-ray source 100, the spectrum of the irradiated X-ray at this time will subsequently be described as a first spectrum.

X-rays irradiated from the focal point of the X-ray source 100 are applied to the subject 102 placed on the bed top plate 103. The X-rays penetrated through the subject 102 are detected by the X-ray detectors 104. The X-ray detector 104 performs separation to the high energy range and the low energy range according to the energy of incident X-rays as described above. Further, this separation is done by a predetermined number of samplings during 1 view to count the number of X-ray photons incident to the high energy range and the low energy range. The signal acquisition section 108 converts a signal corresponding to each of their numbers of X-ray photons into a digital signal and outputs the same as a count number in each energy range.

Next, the control section 107 rotates the gantry rotating section 101 in its rotational direction upon such photography to change an irradiation angle of X-rays to the subject 102. Even during this view, its measurement is done as with the previous view, and its measurement result is output as a count number in each energy range. Here, each X-ray generated from the X-ray source 100 may be a pulse X-ray synchronized with the view or may be continuous X-rays. Further, the photography is repeatedly performed by changing a focal position for each view while causing the rotating and driving to be performed in this way to thereby acquire digital signals corresponding to 360° degrees. The photography is done for every 0.4°, for example between plural views.

Next, the spectrum changing section 111 changes, for example, a tube voltage accelerating an electron beam to 80 kV to change the spectrum of each X-ray generated from the X-ray source 100. While separating the spectrum of each X-ray into the high energy range and the low energy range even at this second round photography between the respective views as with the first round, the number of X-ray photons incident to the X-ray detectors 104 is counted and then counted while changing an irradiation angle of each X-ray to the subject 102 to thereby obtain digital data corresponding to 360°. The digital data obtained in this way will subsequently be described as projected data.

Next, the arithmetic section 105 performs predetermined correction processing and arithmetic processing on the projected data acquired by the signal acquisition section 108 to create multi-energy projected data. In the present embodiment, projected data of a density image as the multi-energy projected data is created as one example. Next, the arithmetic section 105 performs reconstruction processing and arithmetic processing on the multi-energy projected data to create a multi-energy image of the subject 102. Further, the arithmetic section 105 in the present embodiment creates an index (hereinafter called a standard material appropriateness determination index or an appropriateness determination index) for determining whether a standard material used for the creation of the multi-energy projected data is appropriate. The created standard material appropriateness determination index can be displayed at the display section 106. Alternatively, it can be used to change the standard material.

Respective embodiments of the processing in the arithmetic section 105 will hereinafter be described.

Embodiment 1

In the present embodiment, in order to determine the appropriateness of a plurality of standard materials used upon creating the multi-energy image, the arithmetic section 105 calculates energy-independent physical quantities (standard material data) for the respective standard materials by using different combinations of CT data, respectively and calculates, as a numeric value, an index determining the appropriateness of the standard materials from similarity of a plurality of the standard material data obtained by the different combinations.

Figure 5:
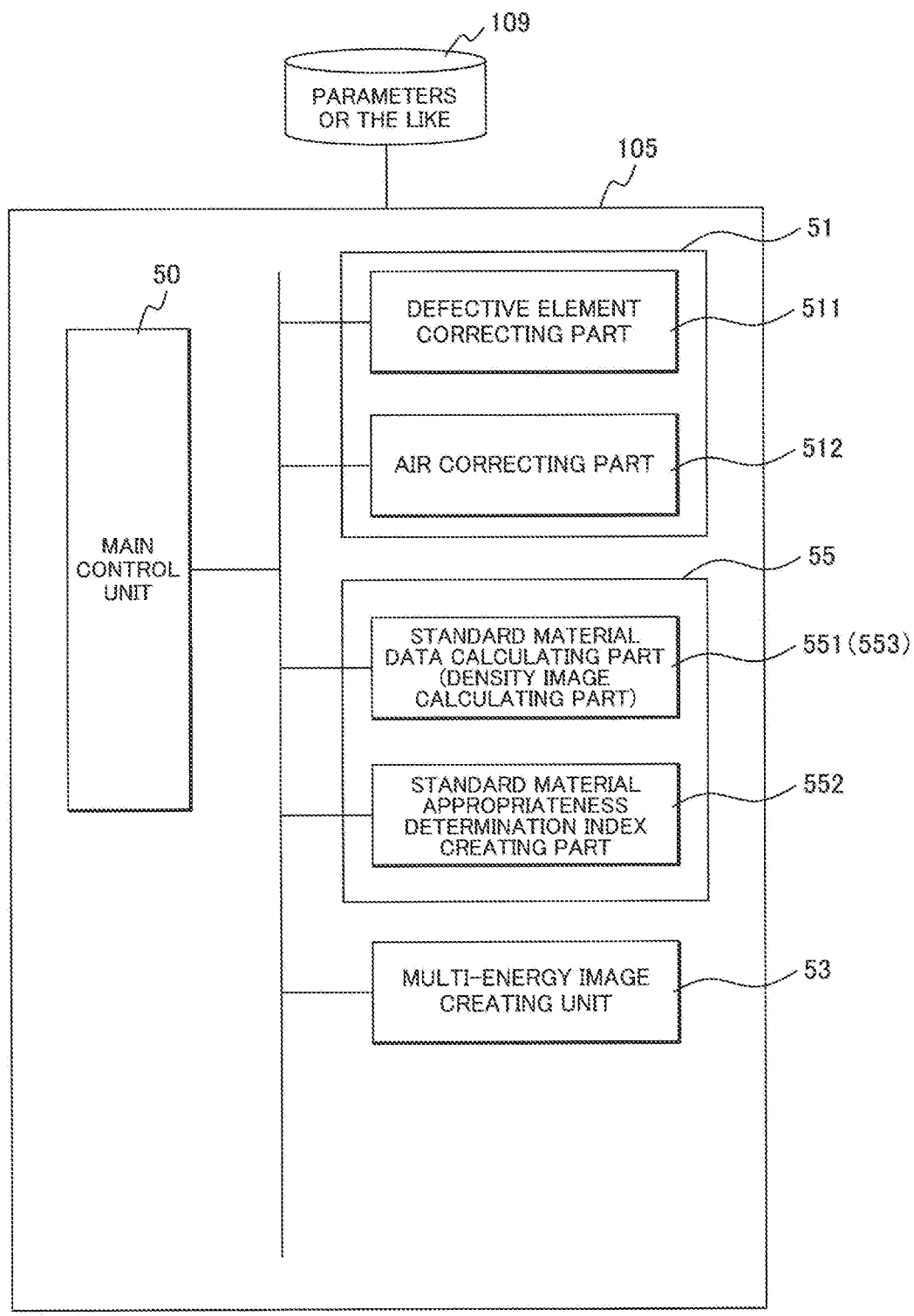
FIG. 5 is a functional block diagram showing a configuration example of an arithmetic section 105 in an embodiment 1.

One example of the configuration of the arithmetic section 105, which realizes the above processing is illustrated in FIG. 5. As shown in FIG. 5, the arithmetic section 105 is equipped with a main control unit 50, a correction processing unit 51, a multi-energy image creating unit 53, and a standard material arithmetic unit 55. The main control unit 50 controls the operations of the correction processing unit 51, the multi-energy image creating unit 53, and the standard material arithmetic unit 55, the transfer of data between the respective units and between the respective units and the storage section 109, etc. The correction processing unit 51 includes a defective element correcting part 511 which corrects data of a defective element in each X-ray detector 104, and an air correcting part 512 which performs an air correction. The multi-energy image creating unit 53 performs operations such as an image reconstruction, the calculation of a density image, a margie-energy operation, etc. by using the projected data corrected by the correction processing unit 51 to create a multi-energy image.

The standard material arithmetic unit 55 is the function of the arithmetic section 105 which performs an arithmetic operation related to a standard material such as the appropriateness of a standard material posited upon dual-image creation, and includes a standard material data calculating part 551 and a standard material appropriateness determination index creating part (hereinafter called an index creating part) 552. FIG. 5 exemplifies where the standard material data calculating part 551 is equipped with a density image calculating part 553 which calculates projected data of a density image as standard material data.

Parameters and data used for the calculation of each unit in the arithmetic section 105 are stored in the storage section 109. The arithmetic section 105 reads the parameters or the like from the storage section 109 if necessary and performs calculations of correction processing, determining processing, arithmetic processing, an image reconstruction, etc. The parameters and data include, for example, data for calculation (140 in FIG. 6) or the like such as an X-ray spectrum distribution, mass absorption coefficient data, etc. used in a defective element position map (141 in FIG. 6) used by the defective element correcting part 511 and an X-ray sensitivity distribution and an X-ray distribution (142 in FIG. 6) used by the air correcting part 512, and used when the density image calculating part 553 calculates the projected data of the density image and the multi-energy image creating unit 53 creates the multi-energy image.

One example of the data processing executed in the arithmetic section 105 will next be described using a flow of FIG. 6.

<Defective Element Correction S601>

Figure 6:
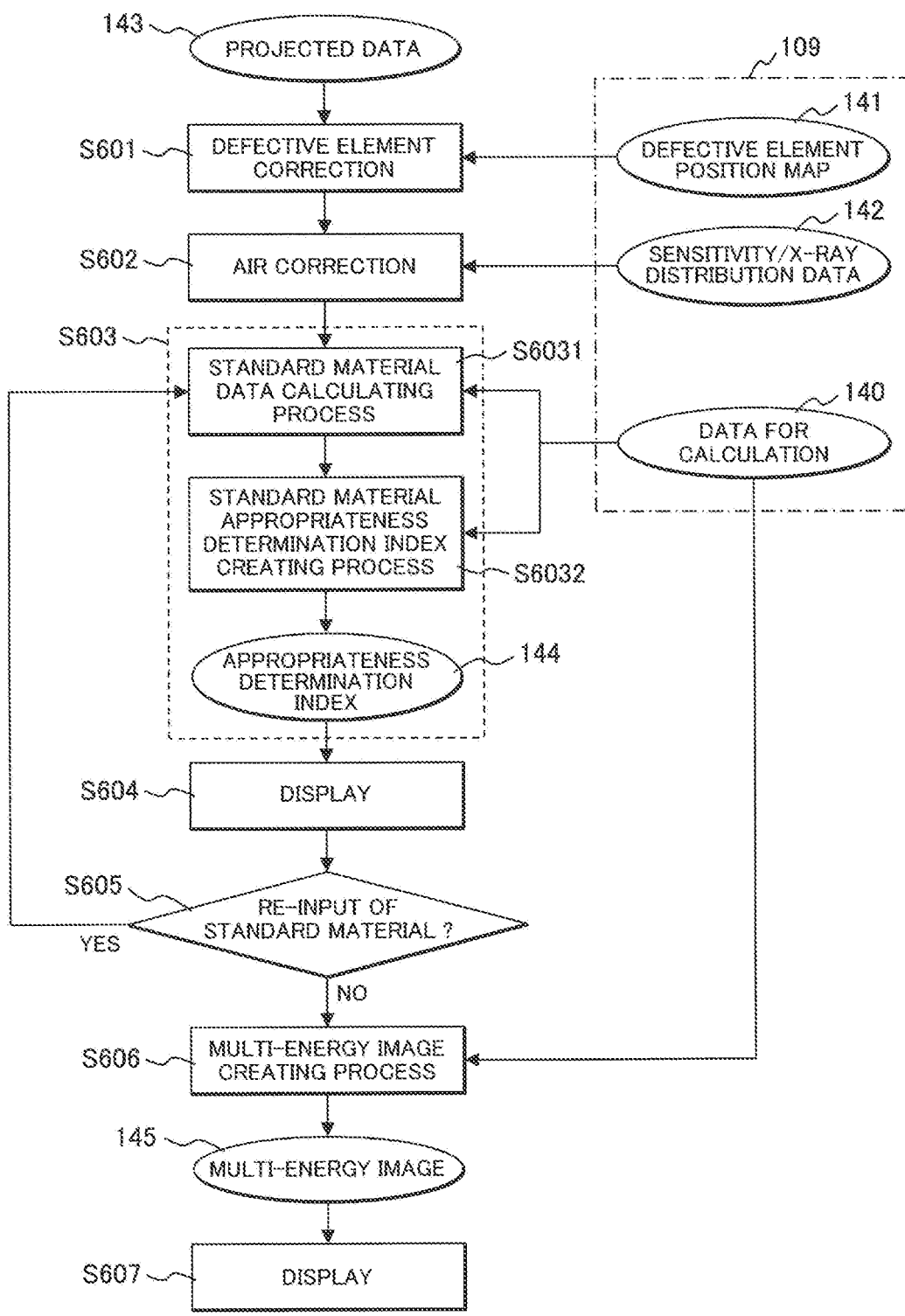
FIG. 6 is a diagram showing one example of a flow for data processing in the embodiment 1.

As shown in FIG. 6, the arithmetic section 105 first performs a defective element correction S601 on the projected data 143 received from the signal acquisition section 108 at the defective element correcting part 511. This correction is, for example, a process for specifying a defective X-ray detecting element (defective element) based on the defective element position map 141 measured and created before a main photographing and stored in the storage section 109, and estimating its output value. A method of estimating the output value is to calculate an average value by using output values of normal X-ray detecting elements 400 around the defective element, for example, and setting the value as the output value of the defective element.

<Air Correction S602>

Next, the air correcting part 512 performs an air correction S602. This correction is realized by, for example, dividing the projected data by the sensitivity/X-ray distribution data 142 measured and created before the main photographing and stored in the storage section 109. The sensitivity/X-ray distribution data 142 is created for every energy range. A method of creating the sensitivity/X-ray distribution data is to, for example, irradiate X-rays from the X-ray source 100 to acquire projected data 143 for every energy without providing the subject 102 and after the defective element correction S601 is performed on them, perform additional averaging thereof in a view direction for every X-ray detecting element 400, and normalize and create them by an average value of the outputs from the X-ray detectors 104.

These correction processes S601 and S602 are performed for every projected data 143 acquired based on their energy ranges and irradiated X-ray spectra.

<Index Creating Process S603>

Next, the standard material arithmetic unit 55 performs an index creating process S603. This process consists of a standard material data calculating process S6031 executed by the standard material data calculating part 551 as a premise, and a standard material appropriateness determination index creating process S6032 executed by the index creating part 552 using the calculated standard material data. The standard material data is a physical quantity of a standard material which does not depend on the energy. In processes to be described below, projected data of a density image of a standard material is calculated as the standard material data. Therefore, the density image calculating part 553 first performs a density image calculating process (standard material data calculating process) S6031.

<<Standard Material Data Calculating Process S6031>>

In the standard material data calculating process S6031, the projected data of the density image of each standard material is calculated from the physical quantity of the set material stored in the calculation data 140 and the projected data. The standard material is specified when being input at the input section 110 before the photographing, for example.

One example of a method for calculating the projected data of the density image will be described. The projected data (photographed image of each X-ray detector) used for calculation are projected data (in which the number of projected data obtained assuming that the kind of spectrum is defined to be p kinds, and the energy range is defined to be q pieces becomes p×q) in a plurality of energy ranges, which are respectively acquired for a plurality of spectrum types. These projected data are used to calculate projected data of density images of plural standard materials.

Here, for ease of explanation, a description will be made about a case where the kind of spectrum is two in number, the energy range is two in number, and the standard material is two in number. At this time, the energy range is described as a (where a becomes H when it is high energy and L when it is low energy). The kind of spectrum is described as b (where b is 1 in the case of a first irradiated X-ray and 2 in the case of a second irradiated X-ray). The value of projected data of each X-ray detecting element 400 where the energy range is a and the kind of spectrum is b is described as $P_{ab}$. The number of photons of energy $\varepsilon$ at the irradiated X-ray (i.e., irradiated X-ray spectrum distribution) is described as $S_b(\varepsilon)$.

Further, the standard material is defined as two kinds of a standard material 1 and a standard material 2. A mass absorption coefficient (mass attenuation coefficient) of each material is described as $\mu m_n(\varepsilon)$ (where n is an integer of 1 or 2 and indicates which standard material is taken). The density thereof is described as $\rho_n$, and projected data of a density image of a standard material n is described as $\delta_n$. The projected data $\delta_n$ of the density image is one obtained by integrating the density of a standard material n being in a path from the focal point to the target X-ray detecting element 400. This can be written like a formula (1).

[Formula 1]

$$\delta_n = \int \rho_n(r) ds \quad (n=1,2) \tag{1}$$

In the formula (1), r indicates the position in the above path.

On the other hand, as the projected data detected by each X-ray detecting element 400, there exist projected data $P_{H1}$, $P_{H2}$, $P_{L1}$ and $P_{L2}$ four in total, which consist of two projected data obtained in the high energy range and the low energy range by using the first irradiated X-ray, and two projected data obtained in the high energy range and the low energy range by using the second irradiated X-ray.

For example, consider the projected data $P_{H1}$ in the high energy range (a=H) obtained with the first spectrum (b=1). First, it is understood that since the X-ray (irradiated X-ray spectrum distribution $S_1$) irradiated with the first spectrum is obtained by being attenuated by the standard material 1 and the standard material 2, the number of photons $T_1$ of a transmitted X-ray of certain energy $\varepsilon$ can be written like a formula (2).

[Formula 2]

$$T_1 S =_1(\varepsilon) \cdot \exp[-\mu m_1(\varepsilon)\delta_1 - \mu m_2(\varepsilon)\delta_2] \tag{2}$$

Since the projected data $P_{H1}$ in the high energy range is one obtained by adding the photon numbers T of the transmitted X-ray in the high energy range, it can be written like a formula 3.

[Formula 3]

$$P_{H1}=\int_H S_1(\varepsilon)\cdot\exp[-\mu m_1(\varepsilon)\delta_1-\mu m_2(\varepsilon)\delta_2]d\varepsilon \quad (3)$$

Here, $\int_H$ means the integration of the high energy range.

When considered in like manner, it is understood that the value $P_{ab}$ of projected data of each X-ray detecting element 400 where the energy range is a and the kind of spectrum is b can be written like formulas (4-1) to (4-4) (hereinafter collectively called a formula (4)). Here, means the integration of the low energy range.

[Formula 4]

$$P_{H1}=\int_H S_1(\varepsilon)\cdot\exp[-\mu m_1(\varepsilon)\delta_1-\mu m_2(\varepsilon)\delta_2]d\varepsilon \quad (4\text{-}1)$$

$$P_{L1}=\int_L S_1(\varepsilon)\cdot\exp[-\mu m_1(\varepsilon)\delta_1-\mu m_2(\varepsilon)\delta_2]d\varepsilon \quad (4\text{-}2)$$

$$P_{H2}=\int_H S_2(\varepsilon)\cdot\exp[-\mu m_1(\varepsilon)\delta_1-\mu m_2(\varepsilon)\delta_2]d\varepsilon \quad (4\text{-}3)$$

$$P_{L2}=\int_L S_2(\varepsilon)\cdot\exp[-\mu m_1(\varepsilon)\delta_1-\mu m_2(\varepsilon)\delta_2]d\varepsilon \quad (4\text{-}4)$$

Since the density does not depend on the energy, the projected data $\delta_n$ of the density image of the standard material originally becomes the same in the case of the high energy range and the low energy range. However, when the standard material is not the same as an actual subject, the projected data $\delta_n$ of the formula (4) assuming the physical quantity of the standard material specified through the input section may vary depending on the energy range.

Assuming that the projected data of the density image of the standard material n (n=1,2) calculated from the formulas of the projected data ($P_{H1}$ and $P_{H2}$) in the high energy range is represented as $\delta_{Hn}$, the projected data calculated from the formulas of the projected data (, $P_{L1}$ and $P_{L2}$) in the low energy range is represented as $\delta_{Ln}$, and they are described while distinguishing them from each other, the formula (4) can be written like formulas (5) ((5-1) to (5-4)). $\delta_{H1}$ and $\delta_{H2}$ are calculated from the formulas (5-1) and (5-3), and $\delta_{L1}$ and $\delta_{L2}$ are calculated from (5-2) and (5-4).

[Formula 5]

$$P_{H1}=\int_H S_1(\varepsilon)\cdot\exp[-\mu m_1(\varepsilon)\delta_{H1}-\mu m_2(\varepsilon)\delta_{H2}]d\varepsilon \quad (5\text{-}1)$$

$$P_{L1}=\int_L S_1(\varepsilon)\cdot\exp[-\mu m_1(\varepsilon)\delta_{L1}-\mu m_2(\varepsilon)\delta_{L2}]d\varepsilon \quad (5\text{-}2)$$

$$P_{H2}=\int_H S_2(\varepsilon)\cdot\exp[-\mu m_1(\varepsilon)\delta_{H1}-\mu m_2(\varepsilon)\delta_{H2}]d\varepsilon \quad (5\text{-}3)$$

$$P_{L2}=\int_L S_2(\varepsilon)\cdot\exp[-\mu m_1(\varepsilon)\delta_{L1}-\mu m_2(\varepsilon)\delta_{L2}]d\varepsilon \quad (5\text{-}4)$$

The projected data $\delta_{Hn}$ and $\delta_{Ln}$ of the density image are calculated with respect to all X-ray detecting elements.

<<Standard Material Appropriateness Determination Index Creating Process S6032>>

Next, the standard material appropriateness determination index creating process S6032 is performed. In this process, the index creating part 552 calculates a standard material appropriateness determination index (hereinafter called an appropriateness determination index or simply a determination index) for whether the standard material is appropriate, by using the projected data $\delta_{Hn}$ and $\delta_{Ln}$ calculated by the density image calculating process (standard material data calculating process) S6031. Here, as the determination index, similarity between the two projected data (probability that they are the same) calculated from the formulas different for the same standard material is calculated.

As the probability calculated by this process becomes higher as will be described below, it can be said that the probability that the standard material is the same as the material of the actual subject is high. This can be defined as the appropriateness determination index.

That is, since the density does not depend on the energy except for errors due to noise where the standard material is the same as the material of the actual subject, it is considered that projected data $\delta_1$ calculated from any two formulas in the formula (4) also become the same ($\delta_{H1}=\delta_{L1}$), and likewise, projected data $\delta_2$ ($\delta_{H2}=\delta_{L2}$) calculated from any two formulas also become the same. On the other hand, when the standard material is different from the material of the actual subject, they are not the same.

This can be understood even from the fact that when, for example, only the standard material 1 is a material (defined as a material A) different from the material of the subject, and the material A is set at approximately the same mass absorption coefficient as the standard material 1 in the high energy range, but greatly varies in the case of low energy, the projected data $\delta_1$ of the density image obtained in the standard material 1 becomes the same as projected data of an density image of the material A when the two formulas obtained in the high energy range are used, whereas when the two formulas obtained in the low energy range are used, the projected data $\delta_1$ of the density image obtained in the standard material 1 becomes a value different from the projected data of the density image of the material A. In other words, when projected data of density images calculated from a set of the different two formulas in the formula (5) coincide with each other, there is a high probability that the standard material is a material which is similar to the material of the subject or the same as that.

Here, when the similarity or coincidence between the projected data of each density image are determined, the data is required to consider having a spread because noise exists in the data. Therefore, the projected data of the density image is represented by a probability distribution of values that it can acquire, to determine a probability that contrasted data are the same. Specifically, the projected data of one X-ray detecting element calculated in the formula (5) is represented as a Gaussian function in which the value of the projected data is defined as a center value, the spread of its distribution is defined as a noise level, and the height thereof is standardized. The noise level is calculated by using, for example, the values of projected data of each density image at its X-ray detecting element and the X-ray detecting elements therearound.

Figure 7:
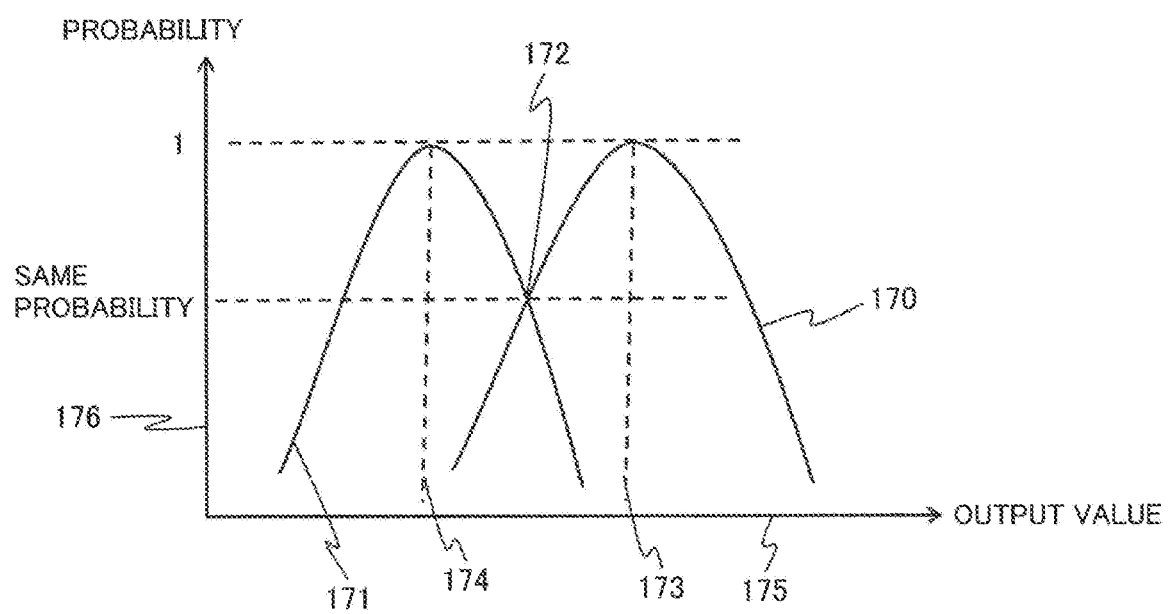
FIG. 7 is an explanatory diagram for describing one example of a method for determining the same probability in the embodiment 1.

FIG. 7 is a graph showing probability distributions of the projected data created in this manner. A curve 171 is a curve obtained from the projected data $\delta_{H1}$ of the density image of the standard material 1 in the high energy range, and a curve 170 is a curve obtained from the projected data $\delta_{L1}$ of the density image of the standard material 1 in the low energy range. The heights of the curves 170 and 171 decided in this way can respectively be regarded as a probability of taking their output values. Therefore, the height of an intersection 172 of the curves 170 and 171 can be regarded as a probability that the curves 170 and 171 are the same, i.e., the output values of the projected data of their density images are identical (hereinafter called the same probability). A probability obtained by determining the same probability over all the X-ray detecting elements and averaging the same is defined as a probability of determining whether the standard material 1 is proper.

Likewise, the same probability is calculated even for the standard material 2. A probability obtained by determining the same probability over all the X-ray detecting elements and averaging the same is defined as a probability of determining whether the standard material 2 is proper. Further, an average value of the probability of the standard material 1 and the probability of the standard material 2 is assumed to be an appropriateness determination index 144.

Incidentally, as a method of calculating the appropriateness determination index 144, the method of calculating the appropriateness determination index 144 from the curves (FIG. 7) in each of which the above-described noise level is created as the spread of the distribution, is one example. No limitation is applied to this when there is provided as an alternative to the curves in FIG. 7, one which can be regarded as the probability distribution of the output values of one X-ray detecting element. Various graphs, curves, distribution maps or data which have been present as prior arts are possible.

For example, a sinogram determined from output values of a plurality of X-ray detecting elements may be used. At this time, the vertical axis indicates the number of X-ray detecting elements brought to the same output value. In this method, however, upon creating the sinogram, the range of an X-ray detecting element to be used is preferably selected while limiting a region uniform in the way the standard material exists.

This is because since the sinogram created in the uniform region becomes a distribution having a spread due to noise centering on the average value of approximately the same output values, the sinogram can similarly be regarded as the probability distribution of the output values obtainable by one X-ray detecting element, and can be regarded to be similar to the probability distribution shown in FIG. 7. On the other hand, a sinogram created in an uneven region becomes one including a difference between output values by the position because the sinogram cannot be regarded as the probability distribution of the output values obtainable by the one X-ray detecting element.

<Display S604>

Figure 8:
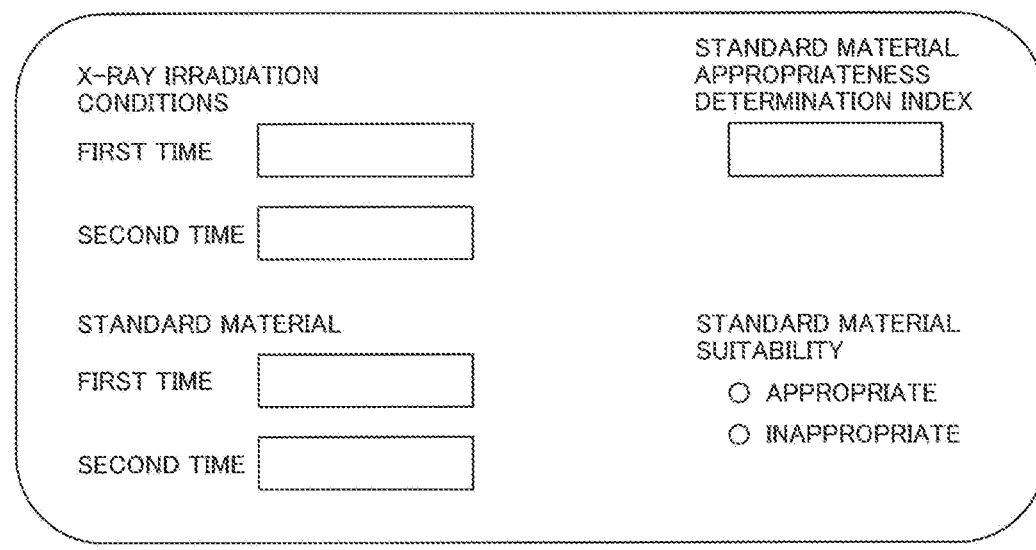
FIGS. 8(a) and 8(b) are respectively a diagram showing an input screen example of a standard material appropriateness determination in the embodiment 1.
Figure 8:
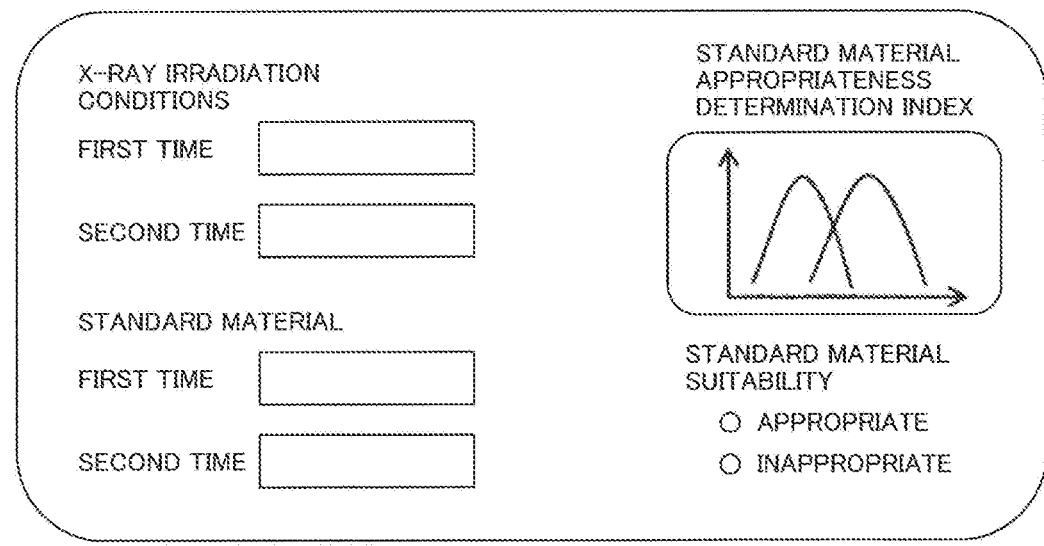

Next, the appropriateness determination index 144 is displayed at the display section 106 (S604). Display examples are shown in FIG. 8. In the example illustrated in FIG. 8(*a*), the appropriateness determination index 144 is displayed as the numeric value of the same probability. Further, in the example shown in FIG. 8(*b*), such a graph as shown in FIG. 7 is displayed. In addition, although not illustrated, various forms are possible as display forms.

A photographer is able to determine while viewing the appropriateness determination index 144 displayed at the display section 106 in this way, whether a standard material is appropriate. In the illustrated examples, the display section 106 doubles as the input section 110 which displays a GUI for performing re-input of a determination result and a standard material by the photographer. It is possible to perform the re-input of the standard material through this GUI. Of course, the input section 110 which inputs the standard material may be separated from the display section 106.

When the photographer determines the standard material not to be appropriate, and the standard material is re-input by the input section 110 (S605), the photographer returns to the index creating process S603, where the standard material data calculating process S6031 and the standard material appropriateness determination index creating process S6032 are performed to recalculate an appropriateness determination index 144. Although a criterion for determining the appropriateness of each standard material is not limited in particular, for example, the appropriateness determination index 144 may be set in such a manner that the standard material is appropriate when the appropriateness determination index 144 is 0.9 or more (probability is 0.9 or more), and inappropriate when less than 0.9.

On the other hand, when it is determined that the standard material is appropriate, the multi-energy image creating unit 53 performs the multi-energy image creating process S606 to create a multi-energy image 145, which is displayed at the display section 106 (S607).

The multi-energy image crating unit 53 reconstructs the projected data of the density image calculated using the appropriate standard material in the standard material data calculating process S6031, for example to create a multi-energy image such as a monochromatic X-ray equivalent image, a standard material density image, an effective atomic number image, an electron density image, a photoelectric effect image, a Compton scattered image, an absorption coefficient image at a spectrum other than the above spectrums used in photography, or the like. A method of creating various multi-energy images is known, and its description will be omitted here.

The configuration of the X-ray CT device according to the present embodiment and the data processing executed in the arithmetic section 105 thereof have been described above. The X-ray CT device according to the present embodiment is equipped with, as the function of the arithmetic section, the standard material data calculating part which calculates the standard material data for the plural standard materials respectively by using the plural CT data acquired in the detection energy ranges of different combinations, and the standard material appropriateness determination index creating part which creates the index for determining the appropriateness of each standard material by using the plural standard material data for the same standard material, which are calculated from the plural CT data of different combinations, whereby it is possible to determine whether the standard material is appropriate, and hence the appropriate standard material can be specified with satisfactory accuracy. Further, it is possible to prevent actually nonexistent materials from being separated in such a manner that they exist. Furthermore, it is possible to improve the quantitativity of quantities such as a calculated density, a presence rate to be shown below, etc.

Although the present embodiment has described the case where the standard material arithmetic unit 55 is mounted within the X-ray CT device, this is one example, but does not limit the present invention. For example, the standard material arithmetic unit 55 may be mounted in the X-ray CT data processing device (hereinafter simply called a data processing device), which is away from the X-ray CT device and processes data of the X-ray CT device.

At this time, the data processing device is equipped with a standard material data calculating part which takes in CT data being projected data acquired in three or more different detection energy ranges and each reconstructed image from X-ray CT device or a storage medium and uses these CT data to separate the same into a plurality of standard materials, and thereby calculates standard material data such as density data of the standard materials, and a standard material determination index creating part which creates an appropriate determination index from the standard material data. Further, the data processing device may be equipped with a CT data storage unit which stores the taken-in CT data therein. The X-ray CT data processing device enables the appropriate determination index to be calculated from the CT data.

Figure 9:
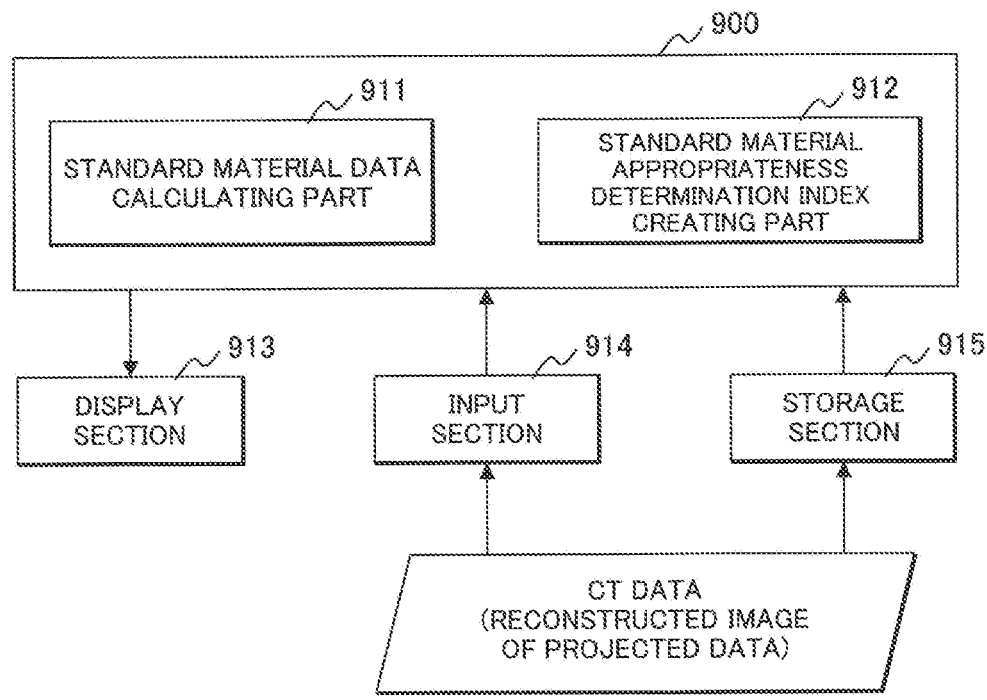
FIG. 9 is a schematic diagram showing an embodiment of an X-ray CT data processing device to which the present invention is applied.

FIG. 9 shows a configuration example of the data processing device. An X-ray CT data processing device 900 shown in the drawing is equipped with, as basic functional parts, a standard material data calculating part 911 and a standard material appropriateness determination index creating part 912. Further, the X-ray CT data processing device 900 may be equipped with a multi-energy creating part (not shown), a determination part which determines the appropriateness of each standard material by using a standard material determination index, etc. These standard material data calculating part 911 and standard material appropriateness determination index creating part 912 are the same in function as the respective parts 551 and 552 of the same names, which are included in the standard material arithmetic unit 55 of the above-described X-ray CT device. The standard material data calculating part 551 and the index creating part 552 of the X-ray CT device described in the present specification will include these corresponding functional parts of the data processing device.

The CT data handled by the present X-ray CT data processing device 900 is CT data before or after correction processing, specifically, data such as projected data, reconstructed images obtained by reconstructing it, etc. These CT data may be input through an input section 914. Alternatively, those acquired by another X-ray CT device may be stored in a storage section 915 by wire, wireless or a portable medium or the like. When the pre-correction processing data is handled, a correction processing part may be provided in the data processing device.

A result of processing by the X-ray CT data processing device 900 is displayed at a display section 913. The display section 913 may be a unique display device provided in the data processing device or may be a display device common to the X-ray CT device having acquired the CT data.

According to such a data processing device, an operator separate from the photographer handling the X-ray CT device is able to process the CT data at a location away from the X-ray CT device or in a time different from that for photography and is also able to feed back its result to the X-ray CT device. Further, the use of such a data processing device also enables the optimum standard material to be decided by execution of its simulation.

Incidentally, the data processing device shown in FIG. 9 is a simple illustration, and some of the elements described in the drawing can be omitted. Moreover, unillustrated elements can also be added. Further, although the CT data is in the storage section 914 in the drawing, this is one example and located in another place like a cloud. The use of this and the like are possible.

[Modification of Embodiment 1]

(Modification of Standard Material Data Calculating Method)

In the embodiment 1, the projected data of each density image calculated as the standard material data is calculated for each energy range. This is, however, one example and does not limit the present invention. For example, the projected data may be calculated for each irradiated X-ray spectrum. Different combinations of energy ranges and irradiated X-ray spectrums may be used in such a manner that the projected data is calculated from the first and four formulas ((5-1) and (5-4)) and the second and third formulas ((5-2) and (5-3)) of the formula (5) respectively. Further, the projected data may always be calculated using the common formulas. That is, the projected data may be calculated while using like the first and second formulas, the first and third formulas, and the first and fourth formulas. Further, without comparing the similarities of the projected data of the two density images in this manner, they may be compared using three or more.

(Modification of Energy Range)

Although each energy range is used as the existing fixed value in the embodiment 1, this is one example and does not limit the present invention. For example, the energy range may be changed according to various photographing conditions such as a tube current, a tube voltage, an X-ray filter, a subject, etc. As one example thereof, the threshold value of low energy or the like is changed such that the width of the energy range of the low energy becomes wide when a large subject is photographed, whereby the energy range may be changed so as to be determined. There are merits such as where since photons of low energy are made extremely smaller than at high energy upon photographing a large subject, the energy range of the low energy is made wide to increase photon numbers, thereby making it possible to improve an SNR (Signal-to-noise ratio), etc.

Further, as another method, the width of a low energy range may be made wide while integrating a plurality of energy ranges of low energy into one and reducing the number of the energy ranges altogether. Further, the number of the energy ranges is reduced, and the number of respective energy ranges may be reset. Further, since photons of low energy are almost lost when a large subject is photographed, the threshold value of the lower limit of the lowest energy may be changed upward, or the lowest energy range may be eliminated. Thus, the speed-up of processing is made possible by reducing the energy range in this manner.

Further, a user may perform selection/determination. Furthermore, the arithmetic section 105 may calculate and determine the optimum energy range.

Thus, when the energy range is selected, determined and changed, it may be affected by the size of the subject as described above. In order to accurately obtain the size of the subject, a pre-scan is performed before the main photographing to acquire a scanogram image and then to estimate the size of the subject, after which it may be used for the selection, determination and change of the energy range.

Also, as a method used for when determining the energy range, for example, SNRs of the respective energy ranges may be determined to be the same degree. When the SNR of one formula in the formula (4) is poor, the accuracy of projected data of a density image, which is determined using this formula is degraded. However, by making the SNRs of the same degree, it is possible to prevent such degradation in the accuracy and set the accuracy of projected data of all density images to the same degree. That is, for example, when the subject size calculated from the scanogram image is large, the energy range is determined to make the low energy range wide, thereby realizing the SNRs of the same degree.

Further, likewise, the dose may also be changed in such a manner that SNRs become similar even at different spectrums. As described previously, since the X-ray photons of low energy are easy to be absorbed more than the photons of high energy when the subject is large, for example, the dose at the photography at a low tube voltage is increased. At this time, however, the dose at a high tube voltage is desirably reduced in such a manner that an exposure dose is not increased.

Also, the method of determining the energy range and the dose is one example and does not limit the present invention. For example, the energy range and the dose may be determined in such a manner that the numbers of X-ray photons incident to the respective energy ranges become the same degree. By determining them in this manner, the SNRs of the respective energy ranges can simply be set to the same degree.

Further, as a method for determining another energy range and dose, for example, the energy range and the dose may be determined in such a manner that CNRs (Contrast-to-noise ratio) of reconstructed images in respective energy ranges become the same degree. When doing in this way, for example, when the density (density image) of each standard material is calculated from a reconstructed image obtained by reconstructing a photographed image as will be described later, an absorption coefficient determined from the reconstructed image is used as indicated by a formula (7), but the accuracy of the density determined from a specific formula can be prevented from degradation by determining the energy range in such a manner that CNRs thereof become the same degree. Further, it is needless to say that the energy range and the dose may be determined by another method.

(Modification of Appropriateness Determination Index)

Although the embodiment 1 has described the case where the appropriateness determination index is determined directly from the standard material data, this is one example and does not limit the present invention. For example, it is possible that the appropriateness determination index is determined from a reconstructed image and projected data created using standard material data. Such data may include multi-energy images such as a density image, a monochromatic X-ray equivalent image, a standard material density image, an effective atomic number image, an electron density image, a photoelectric effect image, a Compton scattered image, an absorption coefficient image at an assumed tube voltage, and their projected data, which can be calculated by using, for example, density data of each standard material, etc. As with the case of the density data even in these, the same probability can be determined, and the appropriateness determination index can be calculated.

Further, the method of calculating the same probability, and the method of calculating the appropriateness determination index from the same probability, which have been described in the embodiment 1 are respectively one example. Various methods are considered. For example, it is possible that the probability is calculated using various verification methods as prior arts. Also, it is possible that the appropriateness determination index is not limited to one, and a plurality of same probabilities are used. For example, although the same probability is averaged with respect to the standard materials 1 and 2 and further all the X-ray detecting elements in the embodiment 1, various cases may be considered such as a case where it is not averaged, a case where it is averaged by some X-ray detecting elements, a case where only the standard materials 1 and 2 are averaged to decide the appropriateness determination index by each X-ray detecting element, a case where a result based on an X-ray detecting element or a standard material worst in probability is used without using the average, etc.

(Modification of Addition, Omission or Order of Processing)

Although the embodiment 1 has described the case where the multi-energy image creating process S606 consists of the reconstructing process and the arithmetic process of creating the multi-energy image, this is one example, but may include at least one of them to create the multi-energy image.

Further, although the defective element correction S601 and the air correction process S602 are carried out as the correction processing in the embodiment 1, this is one example and does not restrict the present invention. For example, when no defective element exists, it is not necessary to perform the defective element correction S601. In a case where a variation in the sensitivity of each X-ray detecting element 400 is small, and the like, it is not necessary to perform the air correction process S602. That is, one or both of these correction processes may not be carried out. Further, for example, other characteristics may be corrected. As such correction, there may be considered, for example, processes such as the correction of the count number by pile-up or polarization, etc. Further, although the correction processing in the present embodiment is carried out before the standard material data calculating process S6031, some or all thereof may vary in correction order as in cases such as being in processing of the standard material data calculating process S6031 or after the processing thereof, and being in processing of the multi-energy image creating process S606 or after the processing thereof, etc.

(Modification of X-Ray Spectrum or The Like)

Although the embodiment 1 has described the case where the two kinds of X-ray spectrums are irradiated and counted in the two energy ranges, and they are separated into the two standard materials, this is one example and does not limit the present invention. It is needless to say that there may be considered various cases in which the X-ray spectrum changing means irradiates two or more kinds of X-ray spectrums, the X-ray detector 104 performs their counting in two or more energy ranges to carry out multi-energy photography, and the arithmetic section 105 separates them into two or more standard materials.

Further, although the embodiment has described the case where the projected data acquired under the conditions different in the irradiated X-ray spectrum and the energy range is calculated, this is one example and does not limit the present invention.

There may also be considered, for example, a case where there are used three or more projected data by being acquired in one energy range with three or more irradiated X-ray spectrums, and there are used three or more projected data by being acquired in three or more energy ranges with one irradiated X-ray spectrum.

That is, there may be considered various cases in which two or more standard material data are calculated for the same standard material using three or more CT data different in spectrum range (hereinafter described as a detection energy range) detected by the X-ray detector to create an appropriateness determination index which serves as an index appropriate for the standard material.

In such a modification, when calculating the projected data of the density image by using the formula (5) in the density image calculating process S6031 in the embodiment 1, for example, the three formulas in the formula (5) can be used. At this time, however, there is a need to make two or more different combinations of more than one in the three formulas. Described by generalization, when p kinds (where p is an integer greater than or equal to 2) of X-ray spectrums are irradiated and counted in q pieces (where q is an integer greater than or equal to 2) of energy ranges, (p×q) projected data are obtained, and the formula (5) can be written by (p×q) formulas. When the number of standard materials is r (where r is an integer greater than or equal to 2), the projected data of the density image can be calculated by using formulas of r or more and (p×q−1) or less.

Embodiment 2

Although the projected data of the density image has been used as the standard material data for calculating the appropriateness determination index 144 in the embodiment 1, the present embodiment is characterized by using data other than projected data, e.g., a density image as standard material data.

Therefore, an arithmetic section 105 (standard material data calculating part 551) of an X-ray CT device or a data processing device according to the present embodiment calculates a density image for each standard material by using a plurality of projected data (data detected by X-ray detectors or data corrected by a correction processing unit 51: collectively called CT data) and sets the same as standard material data. Calculating the same probability of a plurality of density images calculated for the same standard material to create an appropriateness determination index is similar to the embodiment 1 using the projected data.

Figure 10:
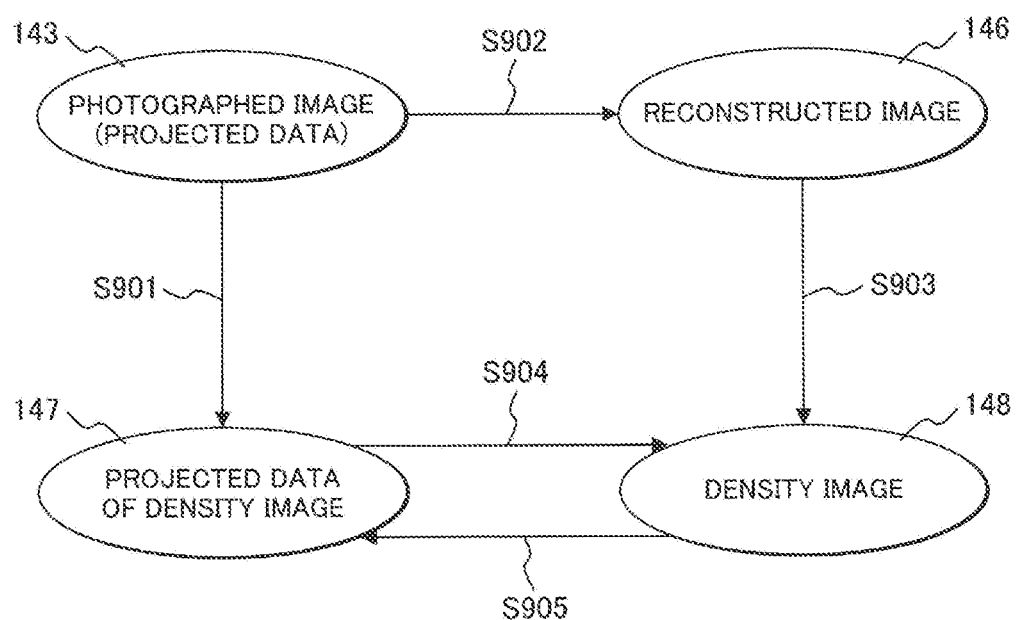
FIG. 10 is an explanatory diagram for describing a method for creating standard material data according to an embodiment 2.

Here, several methods can be adopted as a method of calculating the density image. One method is that as shown in FIG. 10, projected data 147 of a density image is calculated from a photographed image 143 according to a process S901, and the projected data 147 of the density image is subjected to a reconstructing process S904 to create a density image 148. The details of this process S901 are as described in the standard material data calculating process S6031 of FIG. 6, for example, in the embodiment 1. Another method is that a process S902 such as reconstruction is performed on the photographed image 143 being projected data to create a reconstructed image 146, and a process S903 is performed on the reconstructed image 146 to create a density image 148.

Figure 11:
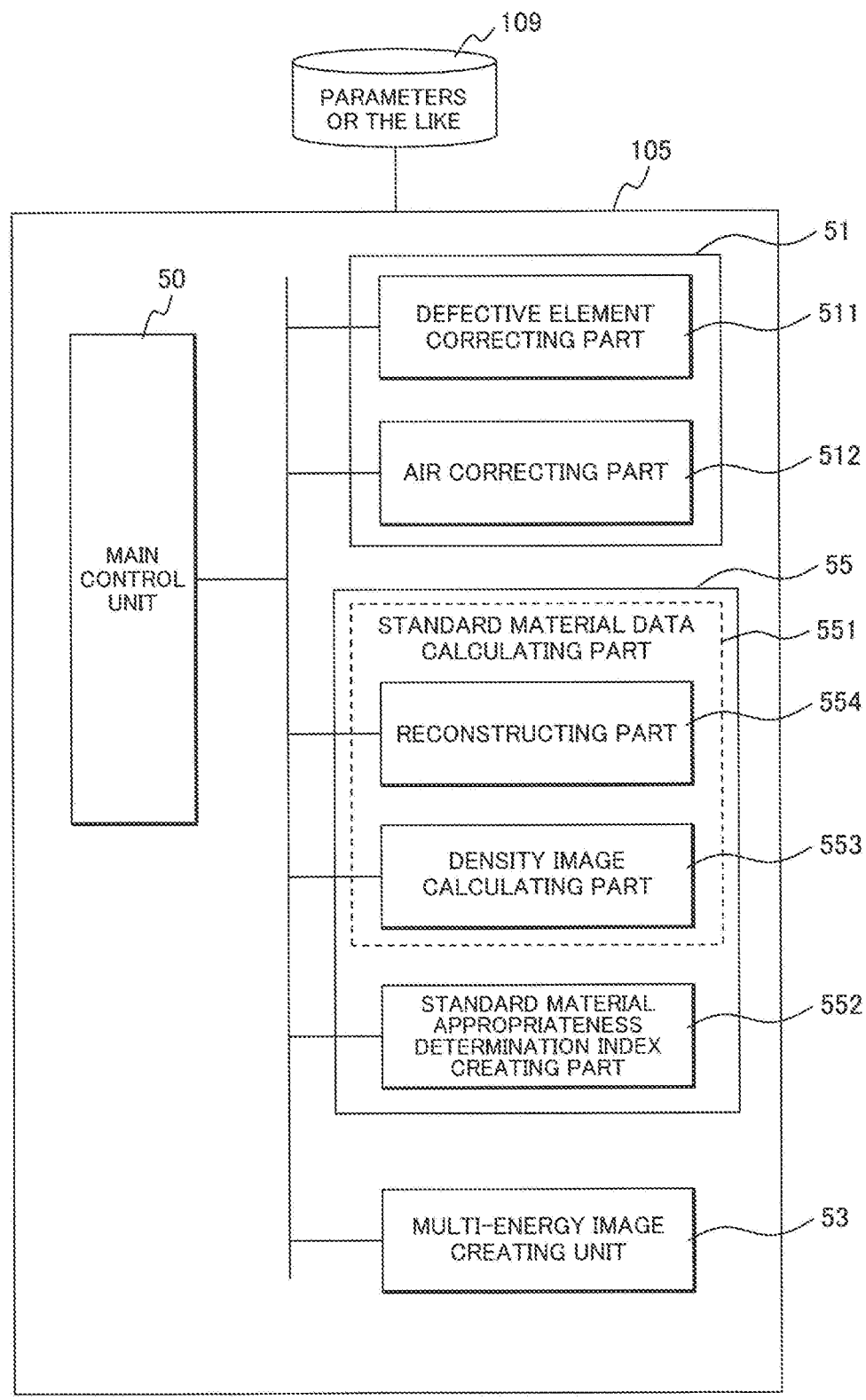
FIG. 11 is a functional block diagram showing a configuration example of an arithmetic section 105 in the embodiment 2.

A configuration example of the arithmetic section 105 where the density image 148 is calculated by the latter method is shown in FIG. 11. In the example illustrated in the drawing, a standard material data calculating part 551 of a standard material arithmetic unit 55 is equipped with a reconstructing part 554 which reconstructs projected data 143 of a photographed image, and a density image calculating part 553 which calculates a density image 148 from a reconstructed image 146. Incidentally, in the case by the former method, the density image calculating part 553 calculates projected data of a density image of a standard material using the projected data 143 (FIG. 10: process S901) as with the embodiment 1 (FIG. 6: standard material data calculating process S6031), and the reconstructing part 554 reconstructs the projected data 147 of the density image (FIG. 10: process S904) to create a density image 148.

A processing procedure of the arithmetic section 105 in the present embodiment is similar to the embodiment 1 except for a density image calculating process. The process of the arithmetic section 105 in the present embodiment will hereinafter be described as appropriate with the aid of FIG. 6 and FIG. 10.

First, correction processes S601 and S602 are performed on the photographed image (projected data) 143, and thereafter, a standard material data calculating process S6031 is performed thereon to calculate a density image 148. This process consists of a process S902 of reconstructing the projected data 143 to create a reconstructed image 146, and a process S903 of creating a density image 148 for each standard material from the reconstructed image 146 as illustrated in FIG. 10.

The process S902 is performed by the known reconstruction technique. The description thereof is omitted, and the details of the process S903 will be described. As with the embodiment 1 even in the following description, a description will be made about a case where projected data separated into two energy ranges of a high energy range and a low energy range and counted respectively with two kinds of irradiated X-ray spectrums by way of example are handled.

For example, the existing calculating method can be applied to the process S903 in dual imaging. In this method, when the effective energies of irradiated X-rays are $E_1$ and $E_2$, and photographing is done with their energies to create a reconstructed image 146, a thus-obtained absorption coefficient (linear attenuation coefficient) $\mu(E_p)$ (where p is an integer of 1 or 2 and indicates the kind of X-ray energy. The same shall apply hereinafter) is represented by a mass absorption coefficient of a standard material. Here, the linear attenuation coefficient and the mass absorption coefficient are also coefficients indicative of the degree of attenuation thereof, whereas the linear attenuation coefficient per unit density is the mass absorption coefficient.

Thus, when the material through which X-rays are transmitted is one kind, the linear attenuation coefficient coincides with the product of the mass absorption coefficient and its density. In the case of two or more materials, the linear attenuation coefficient can be represented as the sum of the products of mass absorption coefficients and densities for each material. Assuming that, for example, standard materials for transmitting materials are defined as two of a standard material 1 and a standard material 2, their mass absorption coefficients are defined as $\mu m_n(E_p)$ (where n is an integer of 1 or 2 and indicates which standard material is available. The same shall apply hereinafter.), and their densities are defined as $c_n$, an absorption coefficient (linear attenuation coefficient) $\mu(E_p)$ and a mass absorption coefficient $\mu m_n(E_p)$ can be written like formulas (6-1) and (6-2) (collectively called a formula (6)).

[Formula 6]

$$\mu(E_1) = c_1 \mu m_1(E_1) + c_2 \mu m_2(E_1) \tag{6-1}$$

$$\mu(E_2) = c_1 \mu m_1(E_2) + c_2 \mu m_2(E_2) \tag{6-2}$$

The mass absorption coefficient is a quantity determined by a material. This is a quantity whose value is obtained by a literature or simulation if what the material is, and the energy of each X-ray that interacts with the material are determined. Thus, when the spectrum of an irradiated X-ray with each effective energy and a standard material are determined, the mass absorption coefficient $\mu m_n(E_p)$ can be determined. The spectrum of each irradiated X-ray at the effective energy can be determined by simulation or the like if, for example, a tube voltage of an X-ray tube, etc. are determined.

In the present embodiment, there is made the counting by the separation into the two energy ranges of the high energy range and the low energy range with each irradiated X-ray spectrum, and four formulas each related to the absorption coefficient are obtained. At this time, since the density $c_n$ can be determined if at least two formulas are provided where the number of standard materials is two, the density can be decided and determined in each of the high energy range and the low energy range, for example. Thus, assuming that $c_{1L}$ and $c_{2L}$ are the densities of the standard material 1 and the standard material 2 in the low energy range, and $c_{1H}$ and $c_{2H}$ are the densities of the standard material 1 and the standard material 2 in the high energy range, the absorption coefficients of the standard materials can be written like a formula (7)((7-1) to (7-4)) using the densities and mass absorption coefficients.

[Formula 7]

$$\mu(E_{1H}) = c_{1H} \mu m_1(E_{1H}) + c_{2H} \mu m_2(E_{1H}) \tag{7-1}$$

$$\mu(E_{2H}) = c_{1H} \mu m_1(E_{2H}) + c_{2H} \mu m_2(E_{2H}) \tag{7-2}$$

$$\mu(E_{1L}) = c_{1L} \mu m_1(E_{1L}) + c_{2L} \mu m_2(E_{1L}) \tag{7-3}$$

$$\mu(E_{2L}) = c_{1L} \mu m_1(E_{2L}) + c_{2L} \mu m_2(E_{2L}) \tag{7-4}$$

As described above, since $\mu m_n$ ($E_p$) being the mass absorption coefficient of the standard material n obtained with each effective energy $E_p$ can be determined using the spectrum of each irradiated X-ray in each of the energy ranges of each effective energy, and the mass absorption coefficient obtained from the literature and simulation, the formula (7) can be solved so that the densities $c_{1L}$, $c_{1H}$, $c_{2L}$ and $c_{2H}$ can be determined, whereby a density image of the standard material is obtained. That is, a density image being two standard material data with respect to one standard material is obtained.

Next, the similarity of $c_{1H}$ and $c_{1L}$ and/or $c_{2H}$ and $c_{2L}$, of the density image determined in the above-described manner is obtained to determine an appropriateness determination index 144 (S6032). As the index indicative of the similarity, for example, the above-mentioned same probability can be used. In this case, as the value of the density image, the value of a predetermined position, an average value, the maximum value, etc. can be appropriately selected. Further, there can be provided a distribution considering noise.

Displaying the appropriateness determination index 144 at the display section 106 (S604), and determining the appropriateness of the standard material on the basis of the displayed appropriateness determination index and repeatedly performing the resetting and appropriateness determination of the standard material as needed (S605) are similar to those in the embodiment 1. Thus, an effect similar to that of the embodiment 1 is obtained.

[Modification of Density Image Calculating Method]

Although there has been described above the case where the density image is used as the standard material data, a process S905 such as a forward projecting process is performed on the density image 148 of the standard material calculated by performing the processes S902 and S903 shown in FIG. 10 to calculate projected data 147 of the density image. This may also be used as standard material data. The projected data 147 of the density image of the standard material is substantially the same as the projected data 147 of the density image created by the process S901 from the photographed image 143 in the embodiment 1 although being different in calculation method, and is similarly used for the appropriateness determining process.

[Modification of Standard Material Data]

Further, the standard material data may use other than the density image and the density data being its projected data. As one example thereof, there may be mentioned, for example, the presence rate of the standard material. Here, the presence rate is a value indicative of how much material exists within a voxel of a reconstructed image. The above-described density $c_n$ of density image is different from the original density (mass/volume) of the material and is one obtained by multiplying the original density of the material by a present rate in the voxel. It is a so-called density of the material in the voxel. Thus, when the density $c_n$ of the standard material in the voxel of the density image can be written like a formula (8) when being represented using a true density $C_n$ of the standard material and its presence rate $\varepsilon_n$.

[Formula 8]

$$c_n = \varepsilon_n C_n \quad (8)$$

Assuming that when considering it as with the case of the density, $\varepsilon_{1L}$ and $\varepsilon_{2L}$ are defined as the presence rates of the standard material 1 and the standard material 2 in the low energy range, and $\varepsilon_{1H}$ and $\varepsilon_{2H}$ are defined as the presence rates of the standard material 1 and the standard material 2 in the low energy range, the formula (7) can be written like formulas (9-1) to (9-4) (hereinafter collectively called a formula (9)).

[Formula 9]

$$\mu(E_{1H}) = \varepsilon_{1H} C_1 \mu m_1 (E_{1H}) + \varepsilon_{2H} C_2 \mu m_2 (E_{1H}) \quad (9\text{-}1)$$

$$\mu(E_{2H}) = \varepsilon_{1H} C_1 \mu m_1 (E_{2H}) + \varepsilon_{2H} C_2 \mu m_2 (E_{2H}) \quad (9\text{-}2)$$

$$\mu(E_{1L}) = \varepsilon_{1L} C_1 \mu m_1 (E_{1L}) + \varepsilon_{2L} C_2 \mu m_2 (E_{1L}) \quad (9\text{-}3)$$

$$\mu(E_{2L}) = \varepsilon_{1L} C_1 \mu m_1 (E_{2L}) + \varepsilon_{2L} C_2 \mu m_2 (E_{2L}) \quad (9\text{-}4)$$

It is understood that since in the formula (9), $\mu m_n$ ($E_p$) indicative of the mass absorption coefficient and the true density $C_n$ of the standard material are values obtained by the literature or simulation as described above, and the absorption coefficient (linear attenuation coefficient) $\mu(E_p)$ is obtained from the reconstructed image, the presence rate $\varepsilon_n$ can be determined.

Further, it is possible that projected data of the presence rate of the standard material is used. This is obtained by forward-projecting the obtained presence rate as with the case of the density image. Such projected data of presence rate can also be assumed to be a length at which a standard material having an assumed density exists in an X-ray path.

As described above, although various physical quantities can be adopted as the standard material data, the physical quantities to be the standard material data are required not to have energy-dependency as understood from the formula (5) and the formula (7). Thus, in the embodiments 1 and 2 and their modifications, the standard material data being data of the physical quantities for each standard material, having no energy-dependency are calculated in plural for the same standard material from the different combinations of the CT data including the projected data and the reconstructed image. The appropriateness determination index is calculated from the similarity (same probability) of those plural standard material data and displayed. Thus, it is possible to determine whether the selected standard material is appropriate.

Embodiment 3

In the embodiments 1 and 2, the index for determining whether the standard material is appropriate is displayed at the display section 106, and the photographer determines the appropriateness of the standard material from the index. The present embodiment is characterized in that a determination is automatically made by an electronic circuit or software. Specifically, a standard material arithmetic unit 55 determines the appropriateness of a standard material on the basis of the value of an index.

The configuration and operation of the present embodiment will be described centering on points different from the embodiment 1.

Figure 12:
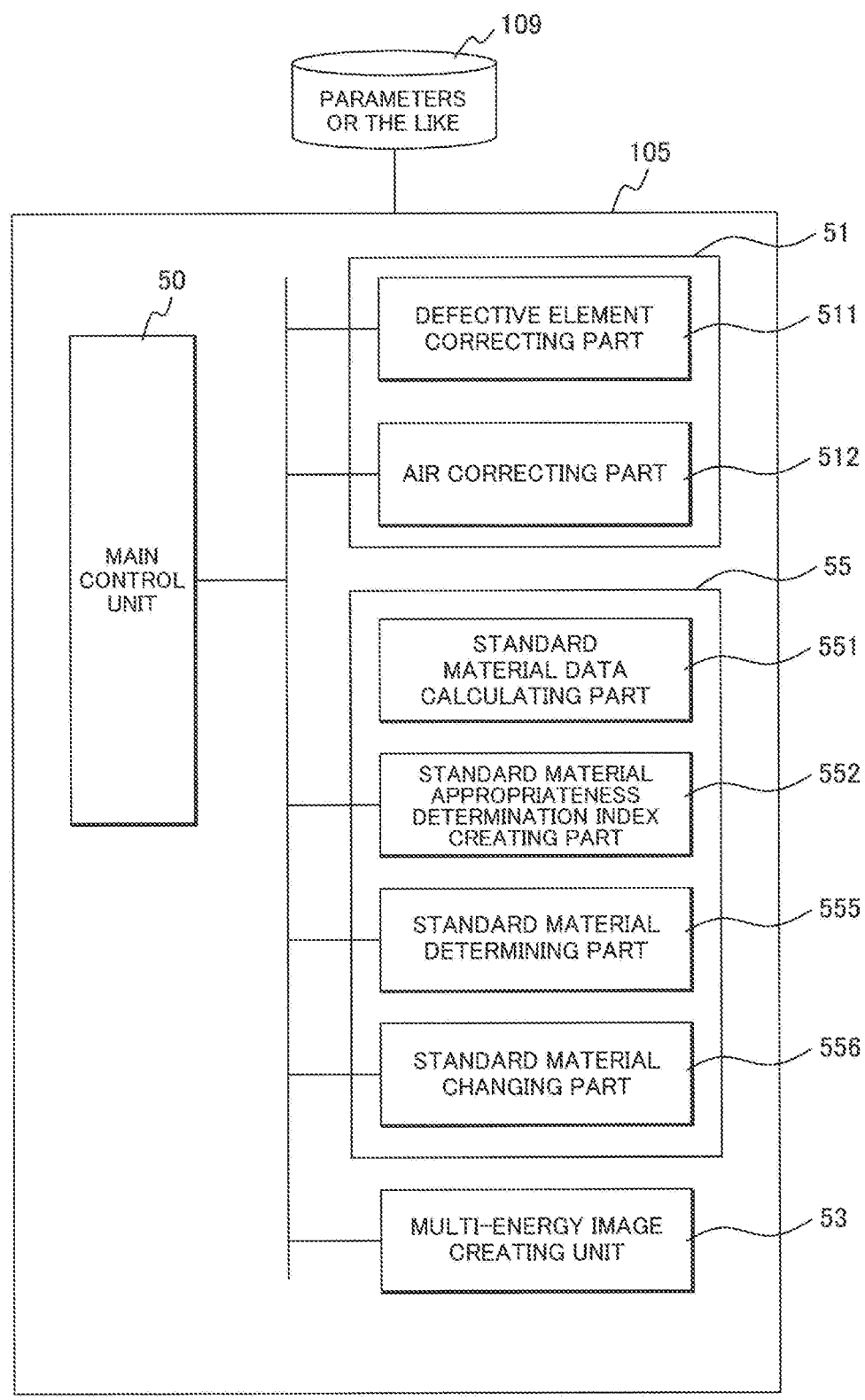
FIG. 12 is a functional block diagram showing a configuration example of an arithmetic section 105 in an embodiment 3.

Even in the present embodiment, the configuration of the device is similar to that of the X-ray CT device shown in FIG. 1, but the configuration of an arithmetic section 105 differs. A configuration example of the arithmetic section 105 is illustrated in FIG. 12. In FIG. 12, the same elements as those in FIG. 5 are denoted by the same signs, and their dual description will be omitted.

A standard material determining part 555 and a standard material changing part 556 are added to the arithmetic section 105 (standard material arithmetic unit 55) in the present embodiment as illustrated in the drawing. These are controlled by a main control unit 50. Further, data such as a threshold value used to determine the appropriateness of a standard material by the standard material determining part 555, etc. are set to a storage section 109 as data 140 for calculation. For example, when an appropriateness determination index is the same probability described in the embodiment 1, for example, a probability 0.9 is set as the threshold value.

Figure 13:
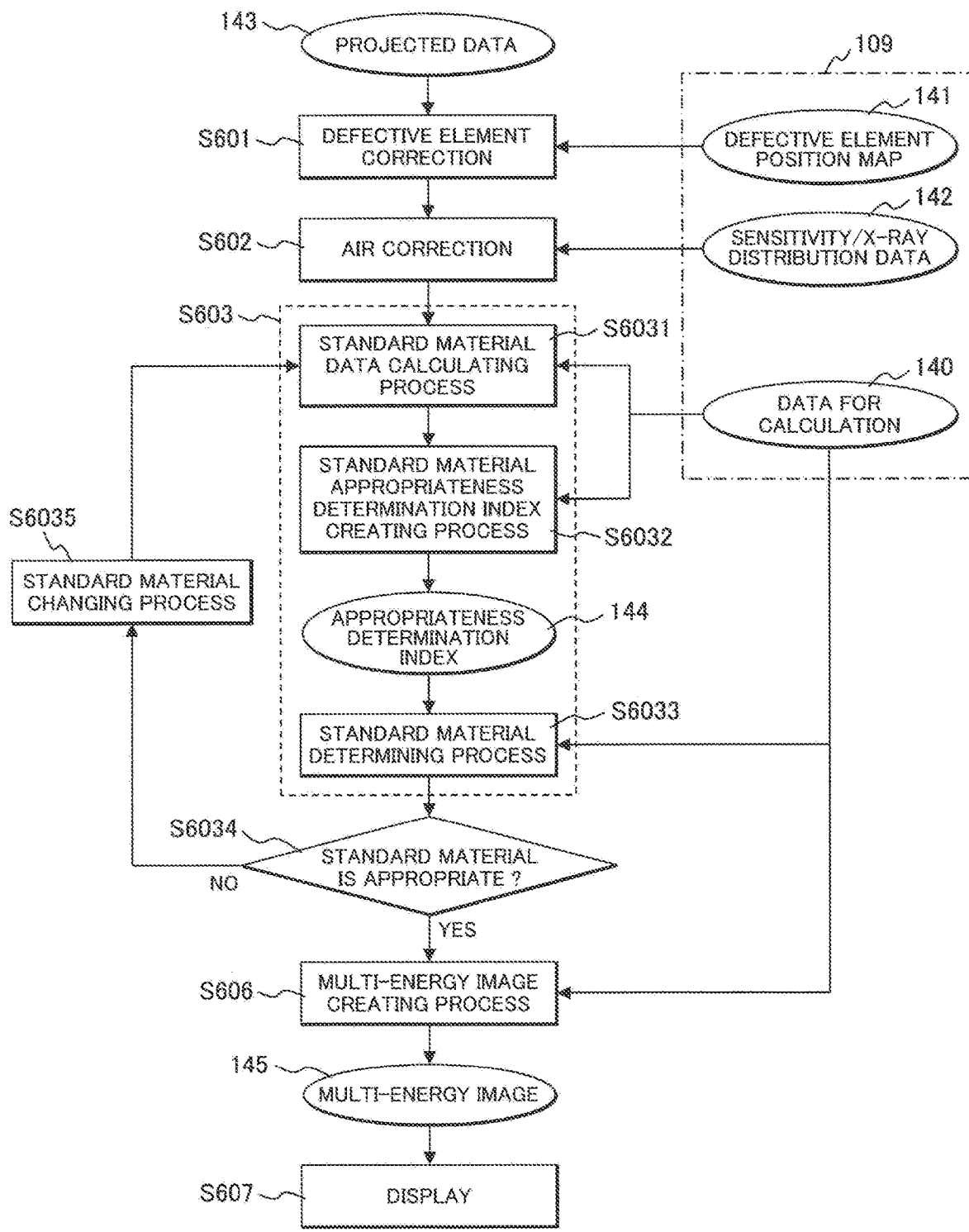
FIG. 13 is a diagram showing one example of a flow for data processing in the embodiment 3.

A process of the present embodiment, principally, a standard material determining process will next be described with reference to a flow of FIG. 13. In FIG. 13, the same processes as those in FIG. 6 are denoted by the same signs, and their dual description will be omitted.

Even in the present embodiment, correcting processes S601 and S602 are performed using projected data 143, and thereafter a standard material data calculating process S6031 and a standard material appropriateness determination index creating process S6032 are performed to create an appropriateness determination index 144.

Standard material data calculated in the standard material data calculating process S6031 is, for example, projected data of a density image of each standard material and a density thereof, and a plurality of data for the same standard material, which are obtained by different combinations of projected data acquired in a plurality of detection energy ranges. Further, the appropriateness determination index 144 created in the standard material appropriateness determination index creating process S6032 is, for example, an index indicative of the similarity between a plurality of standard material data for the same standard material, e.g., the same probability (numeric value) or the like.

When the appropriateness determination index 144 is created, the standard material determining part 555 determines whether the standard material is appropriate (S6033). This determination uses the threshold value in the storage section 109, which is stored as the data 140 for calculation, and is made appropriate when the appropriateness determination index 144 is greater than or equal to the threshold value and is made inappropriate if not so (S6034).

When the determination is made inappropriate, the standard material changing part 556 changes the standard material (S6035) and redo processing from the standard material data calculating process S6031. In the standard material changing process S6035, at least one of the previously-determined standard materials in the standard materials stored in the storage section 109 is changed. Further, it is possible that not only the kind of standard material but also the number of standard materials is changed. The standard material is changed in this manner, and it is repeatedly determined whether the standard material is appropriate.

On the other hand, when it is determined in the determining process S6033 that the standard material is appropriate, a multi-energy image creating process S606 is performed on projected data of its density image to create a multi-energy image 145, which is displayed at a display section 106 (S607). At this time, the name of the standard material determined to be appropriate may be displayed.

Incidentally, although the flow of FIG. 13 has shown the case where changing the standard material after the determining process is also automatically performed, the determination result is displayed at the display section 106, and while viewing it, the photographer may change the standard material.

In this case, each standard material to be a candidate is displayed at the display section 106, and the photographer may select it. In addition, as a method of determining based on an appropriate determination index whether a standard material is appropriate, and a method of changing a standard material, various methods can be adopted without limitation to the above processes.

Further, the modifications which can be adopted in the embodiments 1 and 2 can be applied similarly even in the present embodiment. There can be considered, for example, modifications such as a change of standard material data itself or its calculation method, a change of an X-ray spectrum, detection energy ranges, or the number of types thereof, and a change of an appropriateness determination index, and further, the addition of processing, its omission or a change of its order, etc.

According to the present embodiment, some or all of the appropriateness determination of the standard material and the resetting thereof are made automatic to thereby reduce a burden on the photographer, whereby a more appropriate setting of each standard material can be made. The appropriate setting of the standard material makes it possible to enhance the accuracy of separating CT data into the standard materials as with the embodiment 1.

Embodiment 4

In the embodiment 1, the similarity of the plural standard material data for each standard material, i.e., the probability that they are the same is defined as the appropriateness determination index, and the appropriateness determination index is determined by digitization. In the present embodiment, however, standard material data is represented as a graph and thereby defined to be an appropriateness determination index 144. That is, in the present embodiment, a graphical display itself of a plurality of standard materials to be compared is assumed to be an appropriateness determination index. Even in the present embodiment, so long as physical quantities which do not depend on energy are taken as the standard material data, no limitation is applied thereto. Further, detection energy ranges and the number thereof are also not limited. The following description will however be made about a case wherein as one example, standard material data is a density image, and a plurality of detection energy ranges are realized by three. The present embodiment will hereinafter be described centering on points different from the embodiment 1.

Since the configuration of an arithmetic section 105 in the present embodiment is common to the configuration of the embodiment 2 shown in FIG. 11, it will hereinafter be described as appropriate with the aid of FIG. 11.

As with the case of the embodiment 1, the arithmetic section 105 in the present embodiment has a correction processing part 51 which performs a correction process, a standard material arithmetic unit 55 for creating a standard material appropriateness determination index, and a multi-energy image creating unit 53. A correction processing unit 51 includes a defective element correcting part 511 and an air correcting part 512.

The standard material arithmetic unit 55 calculates a density image 148 of a standard material from a reconstructed image obtained by reconstructing projected data acquired by photography. Therefore, the standard material arithmetic unit 55 includes, as a standard material data calculating part 551, a reconstructing part 554 which performs a reconstructing process, and a density image calculating part 553 which calculates projected data of a density image, as with the embodiment 2. The standard material arithmetic unit 55 is the same as that in the embodiments 1 and 2 in that it includes an index creating part 552. Further, although not illustrated in FIG. 11, the standard material arithmetic unit 55 may be equipped with a standard material determining part 555 and a standard material changing part 556 such as shown in FIG. 12 as with the embodiment 3 when the appropriateness determination and change of the standard material is performed by an electronic circuit or software. Each part of the arithmetic section 105 is operated under the control of a main control unit 50.

Figure 14:
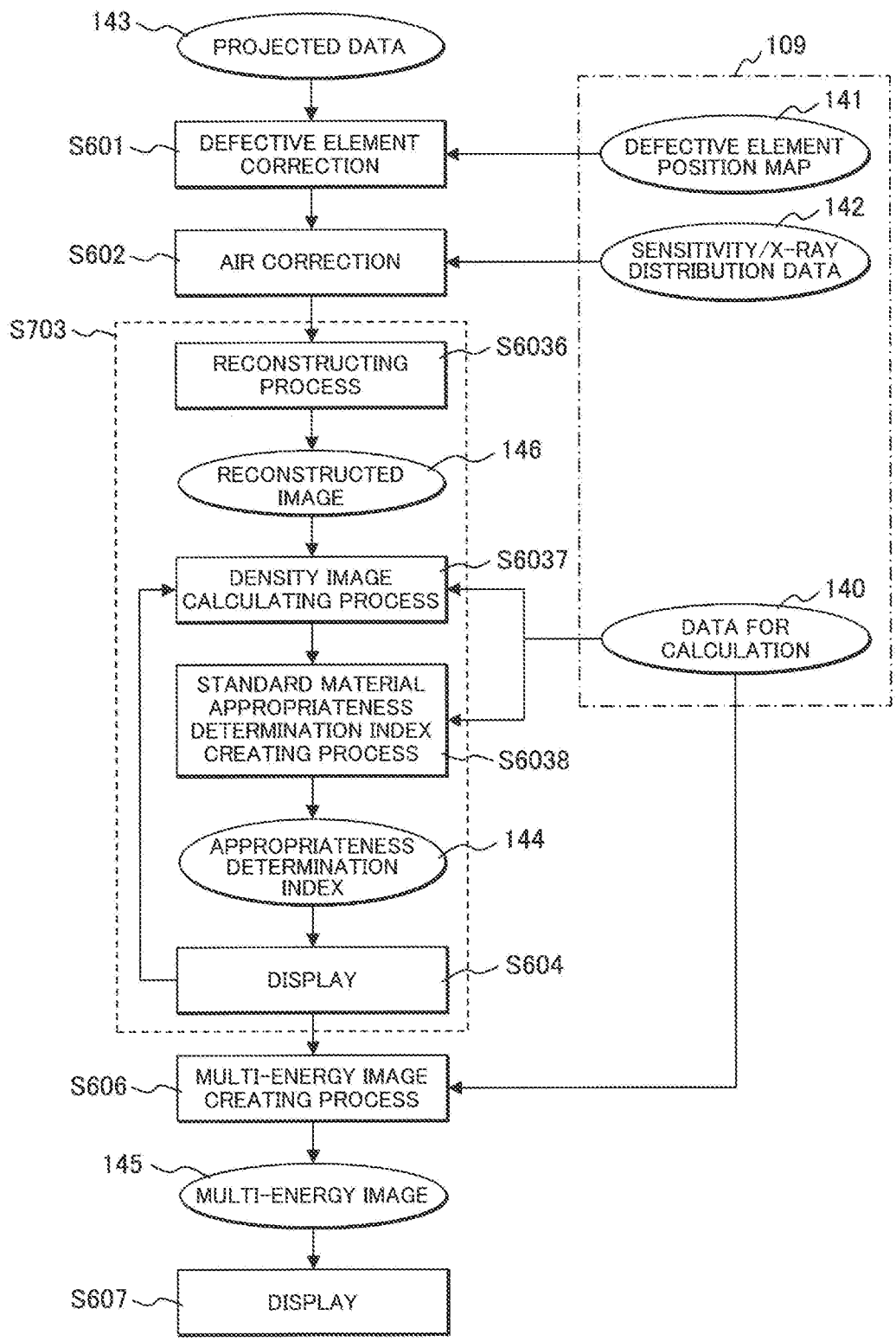
FIG. 14 is a diagram showing one example of a flow for data processing in an embodiment 4.

A flow of data processing executed in the arithmetic section 105 will next be described with reference to FIG. 14. Incidentally, the same processes as those in FIG. 6 or FIG. 13 are denoted by the same signs, and their description will be omitted.

First, a defective correcting process S601 and an air correction S602 are performed on projected data 143 in each energy range. Next, an index arithmetic operation S703 is performed. In this process, first, the reconstructing part 554 performs a reconstructing process S6036 to create a reconstructed image 146.

Next, a density image calculating process S6037 is performed. This process is basically similar to the process (process S903 of FIG. 10) described in the embodiment 2. Since there are however three detection energy ranges in the present embodiment, the density is calculated by setting up three formulas as will be described below.

First, the three energy ranges are described in order of decreasing the energy like a high energy range, a medium energy range, and a low energy range, and subscripts indicating them are assumed to be H, M, and L respectively. A relational formula between a reconstructed image and a density value corresponding to the above-mentioned formula (6) can be written like a formula (10) ((10-1) to (10-3)).

[Formula 10]

$$\mu(E_H) = c_1 \mu m_1 (E_H) + c_2 \mu m_2 (E_H) \tag{10-1}$$

$$\mu(E_M) = c_1 \mu m_1 (E_M) + c_2 \mu m_2 (E_M) \tag{10-2}$$

$$\mu(E_L) = c_1 \mu m_1 (E_L) + c_2 \mu m_2 (E_L) \tag{10-3}$$

Here, $\mu(E_i)$ (where i=H, M, L) indicates the value of a reconstructed image acquired in each of the energy ranges, i.e., an absorption coefficient value (linear attenuation coefficient). $c_n$ (where n is an integer of 1 or 2 and indicates which standard material is available. The same shall apply hereinafter) indicates a density. $\mu m_n (\varepsilon)$ indicates a mass absorption coefficient (mass attenuation coefficient) at energy $\varepsilon$. $E_i$ indicates the energy of each irradiated X-ray.

In the density image calculating process S6037, a plurality of $c_1$ and a plurality of $c_2$ are calculated from these formulas.

This means that, for example, the first $c_1$ and $c_2$ (hereinafter called densities at high energy, which are described $c_{1H}$ and $c_{2H}$) are calculated from the first and second formulas in the formula (10), and the second $c_1$ and $c_2$ (hereinafter called densities at low energy, which are described as $c_{1L}$ and $c_{2L}$) are calculated from the second and third formulas.

Figure 15:
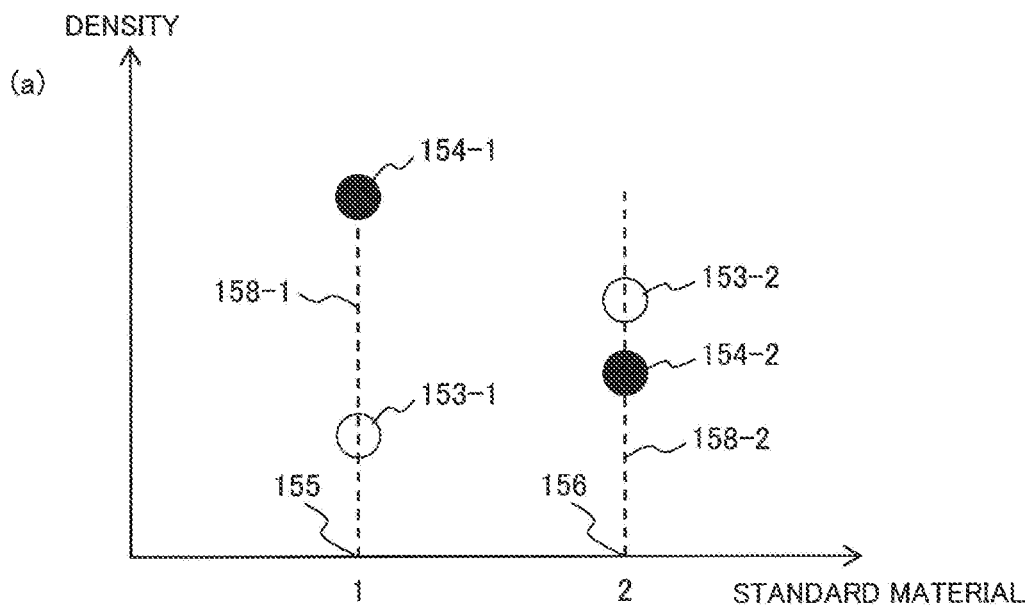
FIGS. 15(a) and 15(b) are respectively one example of a graph displayed as an appropriateness determination index 144 in the embodiment 4 and a diagram showing where a standard material is inappropriate.
Figure 15:
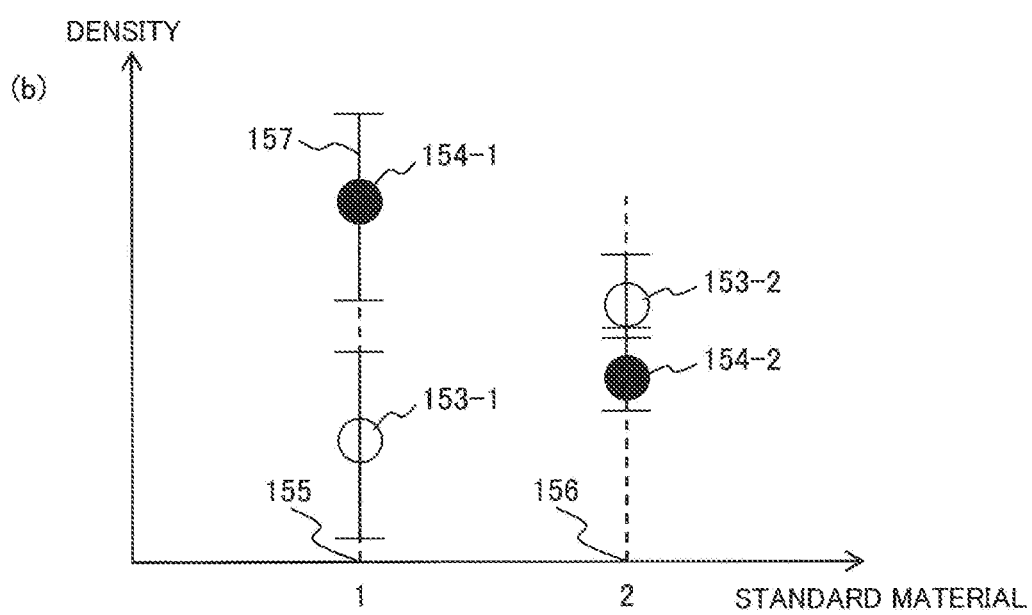

Next, a standard material appropriateness determination index is created (S6038). In this standard material appropriateness determination index creating process S6038, a graph of the densities $c_{1H}$, $c_{1L}$, $c_{2H}$, and $c_{2L}$ is created. This is displayed at a display section 106 as an appropriateness determination index 144 (S604). Although the graph and its display method may include various ones, their examples will be illustrated in FIGS. 15(a) and 15(b). FIG. 15 illustrates graphically the values of densities calculated for each standard material. The vertical axis is a density, and the horizontal axis is an arbitrary scale indicative of a standard material. In the drawing, a position 155 indicates a standard material 1, and a position 156 indicates a standard material 2, respectively. Further, a white circle 153-1 indicates a result of $c_{1L}$, a white circle 153-2 indicates a result of $c_{2L}$, a black circle 154-1 indicates a result of $c_{1H}$, and a black circle 154-2 indicates a result of $c_{2H}$, respectively.

Here, the value of the density can be calculated at a predetermined position in the reconstructed image, but herein, for example, the average value of density images in all regions of the reconstructed image is used. The values of the so-obtained densities may be plotted as the value of one point as illustrated in FIG. 15(a). As illustrated in FIG. 15(b), error bars 157 may be added. In general, noise exists in the acquired data, and each calculated density image has noise. The error bar 157 is a display indicative of a distribution of values due to such noise. The width of the error bar 157 is preferably the same as noise of an image, for example, or defined to be one obtained by multiplying it by a constant.

The result of FIG. 15 is one example of a result where the selected standard material is inappropriate. That is, when the standard material is inappropriate, the values of the densities in the same energy range, which are obtained by two different methods differ. This includes the case where $c_{1L}$ (153-1) and $c_{1H}$ (154-1) are different and the case where $c_{2L}$ (153-2) and $c_{2H}$ (154-2) are different. In the present embodiment, the standard material can be determined to be inappropriate where the densities in both energy ranges are different or the density values in at least one of them differ.

Figure 16:
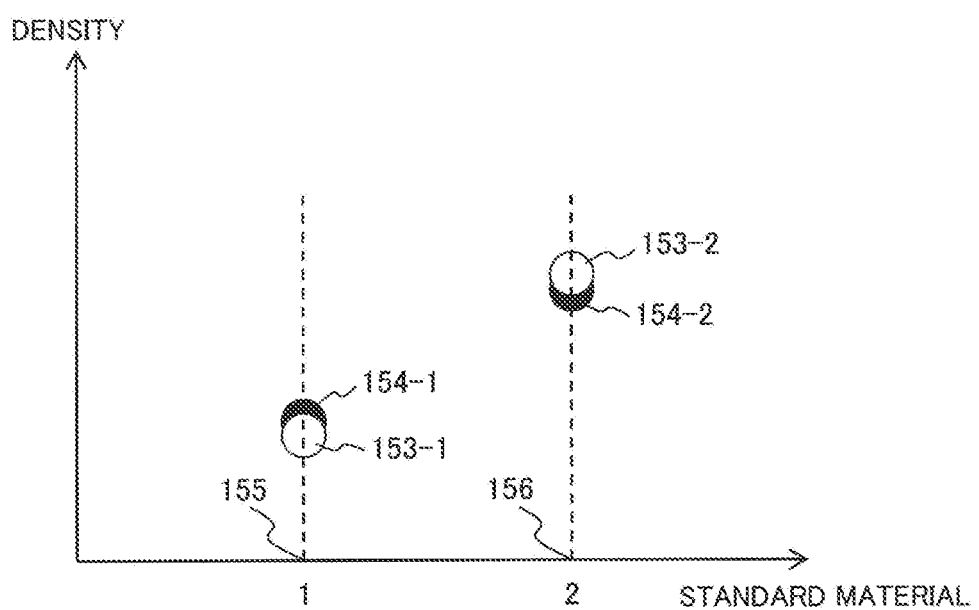
FIG. 16 is one example of a graph displayed as the appropriateness determination index 144 in the embodiment 4 and an explanatory diagram showing where a standard material is appropriate.

On the other hand, when the selected standard material is appropriate, the values of the densities of the same standard material, which are obtained by two different methods coincide with each other as illustrated in FIG. 16, for example. This means that $c_{1L}$ (153-1) and $c_{1H}$ (154-1) coincide with each other, and $c_{2L}$ (153-2) and $c_{2H}$ (154-2) coincide with each other. Since, however, the values of the densities include a distribution due to noise, their coincidences are not required to be complete. In this case, a display showing the value distribution like the error bar 157 shown in FIG. 15(b) is added, so that it becomes easy to determine the coincidence from their overlapping conditions.

Thus, when the selected standard material is appropriate, the values of the densities of the respective standard materials coincide under the same standard material even when calculated using projected data in energy ranges of another combination. This shows that it is understood that, for example, when one standard material is inappropriate, and the calculation of the formula (10) is made using a mass absorption coefficient value in the low energy range, which is different from an actual value, a result calculated using the high energy range and the medium energy range is correct, whereas a result calculated using the low energy range and the medium energy range becomes an incorrect different result, so that they do not coincide.

At such a time, the values of the densities of both the standard material 1 and the standard material 2, which are calculated using the low energy range and the medium energy range both assume incorrect values depending on the mistake of the mass absorption coefficient value of one standard material. However, it is also possible that since mass absorption coefficient values different from actual ones vary in all of the low energy range, the medium energy range, and the high energy range when the standard material is not appropriate in fact, both standard materials assume incorrect values, and only one of the standard materials assumes a correct value. It can however be said that since the mass absorption coefficient values of both standard materials in almost all energy ranges are considered to coincide with those in fact where the results obtained in the energy ranges of both combinations coincide, it is possible to determine whether both standard materials are appropriate.

An appropriate determination index 144 (graph) calculated in the above-described manner is displayed by the display section 106 (S604). The photographer is able to determine while viewing it whether the standard material is appropriate. When the photographer determines the standard material to be inappropriate, the photographer changes the standard material as with the case of the embodiment 1 shown in FIG. 6, for example, and performs the density image calculating process S6037 and the standard material appropriateness determination index creating process S6038 again to determine and display an appropriateness determination index 144 (S604). On the other hand, when the photographer determines the standard material to be appropriate, the photographer performs the multi-energy image creating process S606 using the standard material at the multi-energy image creating unit 53 to create a multi-energy image 145 and displays the same at the display section 106 (S607).

According to the present embodiment as described above, the appropriate standard material can be determined by using the graph of the values of the densities of the standard materials as the appropriateness determination index 144.

Incidentally, the graphs of FIGS. 15 and 16 are simple illustrations. As their display methods, there may be mentioned cases of various kinds, colors, expression methods, etc. Further, it is needless to say that various additional expressions may be applied to the graphs and the error bars. For example, the expressions such as the color, shape and the like of the error bars 157 of $c_{1L}$(153-1) and $c_{1H}$(154-1) may be made different to make it easy to see overlapping of the error bars 157 of $c_{1L}$(153-1) and $c_{1H}$(154-1). On the other hand, it is possible that there are no some expressions such as the absence of a dotted line 158-1 and a dotted line 158-2 in FIG. 15(*a*).

Also, although the present embodiment has described the case where the average value of the reconstructed image in all regions is used as the appropriateness determination index 144, this is one example and dose not limit the present invention. There may be, for example, a value at a predetermined position, and further the maximum value, the minimum value and the average value in the range of the predetermined position and magnitude.

Further, the photographer may determine the position and the magnitude. As its method, there may also be mentioned, for example, methods such as the reconstructed image 146 and the density image 148 obtained by separation being displayed at the display section 106 and being determined.

As with other embodiments described above, the present embodiment can be applied not only to an X-ray CT device, but also to an X-ray CT data processing device being another modality. Further, the modifications illustrated in other embodiments can be applied even to the present embodiment unless there is anything contradictory technically.

[Modification of Embodiment 4]

Several modifications of the embodiment 4 will hereinafter be described.

(Modification of Graph)

Although the embodiment 4 has described the case where the data are displayed in points on the graph, this is one example and does not limit the present invention. There may also be mentioned, for example, cases of other various graphs such as a bar graph, a line graph, etc. Further, there may be not only a case where they themselves are displayed, but also a case where fitting-done functions are displayed, etc. Furthermore, using these functions, their countings and inclinations may be defined as indices for determining whether they are the same.

Although the present embodiment has described the case where as the graph of the appropriateness determination index 144, the density is used for the vertical axis, and the standard material is used for the horizontal axis, this is one example and does not limit the present invention. There may be, for example, a case where the vertical axis and the horizontal axis are made opposite. Further, there may be a case where the horizontal axis is another parameter. There may be, for example, cases such as various representative values indicative of a plurality of types of energy ranges used for density calculation, e.g., the average value, center value and the like of a used energy range, etc.

This may include a case where in the present embodiment, for example, since one density value is determined from the low energy range and the medium energy range, and another is determined from the high energy range and the medium energy range, the horizontal axis assumes the low energy range and the high energy range. Further, other values may be used for the horizontal axis. This may include, for example, a case where the atomic number of each standard material is used, a case where the center value of the low energy range and the center value of the high energy range are used, etc. Further, there may be a case where parameters other than the standard material and the energy are used. There may be a case where the physical quantity of a material or the like is used, and a case where one like a data number other than the physical quantity is used.

Further, there may be a case where the standard material data other than the density is used even for the vertical axis. For example, the various standard material data themselves described in the embodiment 1, and those calculated therefrom may be used. As one example thereof, there may be a case where the presence rate of the standard material is used as described in the embodiment 2. Further, the values of the density, the reconstructed image of the presence rate and the projected data, and further the multi-energy images such as the monochromatic X-ray equivalent image, standard material density image, effective atomic number image, electron density image, photoelectric effect image, Compton scattered image, and absorption coefficient image at the assumed tube voltage, etc., and some or all of their projected data, and further the values obtained therefrom, e.g., the average value and the like may be used for the vertical axis. In the present method, however, since the physical quantities which do not depend on the energy originally are obtained by the two or more methods, and a determination is made as to whether the standard material is appropriate, depending on whether they coincide, the energy-independent physical quantities are required to be used for the vertical axis.

(Modification of Appropriateness Determination Index Other Than Graph)

Further, without using the graph as for the appropriateness determination index 144, the density image being the standard material data and the projected data thereof, the multi-energy images obtained therefrom, and their projected data themselves may be compared as the appropriateness determination index 144. As for these images, for example, in the present embodiment, one is created using $c_{1L}$(153-1) and $c_{2L}$(154-1) being the densities obtained from the low energy range and the medium energy range, and another is created using $c_{1H}$(153-2) and $c_{2H}$(154-2) being the densities obtained from the high energy range and the medium energy range. They are compared as the appropriateness determination index 144. That is, a plurality of multi-energy images and their projected data are created using data in energy ranges of another combination, and they are compared.

(Modification of Method for Calculating Density)

Although in the embodiment 4, the density values are respectively determined using the reconstructed images in the combination of the high energy range and the medium energy range and the combination of the high energy range and the low energy range, this is one example and does not limit the present invention. There may be various cases in which two sets of projected data are selected from the high energy range, the medium energy range and the low energy range.

For example, there may be one case where the density is calculated from the high energy range and the low energy range, and another case where the density is calculated from the medium energy range and the low energy range, etc. Further, it is needless to say that although the three energy ranges are adopted in the present embodiment, three or more energy ranges may be adopted. At this time, there may be various cases in which two sets of projected data are selected from within n pieces (where n is an integer greater than or equal to 3). Further, there may be not only a case where the density values of a set of standard materials are determined from two sets of projected data, but also a case where the density values of a set of standard materials are determined using three or more sets of projected data.

Further, although after obtaining the projected data in each energy range by reconstruction, the value of the density of each standard material is obtained by being subjected to the density image calculating process S6037 in the embodiment 4, this is one example and does not limit the present invention. As shown in FIG. 10, for example, the density image calculating process S901 is performed on the projected data 143 to determine the projected data 147 of the density image. This may be given the reconstructing process S904 to obtain the density image 148.

(Modification of Appropriateness Determination Process)

Although the embodiment 4 has described the case where the photographer performs the appropriateness determination of the standard material on the basis of the determination index (graph or the like) displayed at the display section 106, this is one example and does not limit the present invention. It is needless to say that whether data coincide with each other may be determined using an electronic circuit or may be determined using software through a computer or the like.

Further, although it is determined in the embodiment 4, based on the value of each density at the same energy, whether the standard material is appropriate or not, as with the embodiment 1, for example, the probability that the determined density values at the same energy are the same is calculated, and the standard material may automatically be determined based on the probability. Further, the index indicative of whether the density values being the same is displayed on the graph and may be used as an aid to the determination.

[Embodiment of Display Form]

In the X-ray CT device or data processing device according to each embodiment described above, when the arithmetic section 105 is operated, the arithmetic section 105 appropriately reads data stored in the storage section 109 from the storage section 109 and besides receives information (e.g., standard material data, a numeric value being a result obtained by simulation, etc.) input by the photographer handling the X-ray CT device and the operator (hereinafter both collectively an operator) handling the data processing device from the display section 106/input section 110 to perform various arithmetic operations.

A description will be made about an embodiment of a GUI for smoothly carrying out the reception of such input information.

Figure 17:
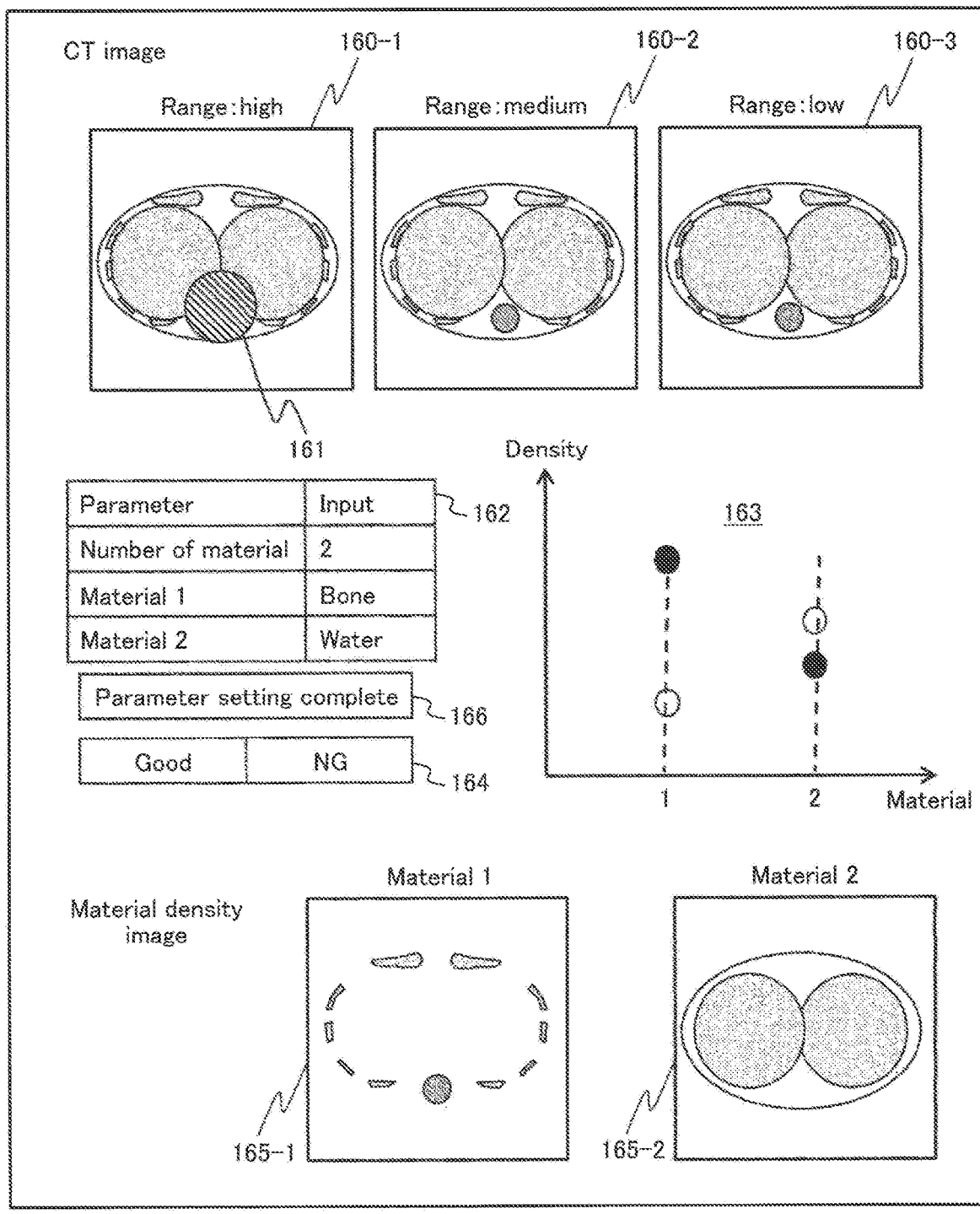
FIG. 17 is a diagram showing one example of a GUI.

One example of the GUI is illustrated in FIG. 17. In FIG. 17, each CT image is, for example, one example in which the reconstructed image 146 created from the photographed image by the reconstructing part 554 is displayed. CT images 160-1, 160-2 and 160-3 are respectively those obtained when the energy range is set to the high energy range, the medium energy range and the low energy range.

A region 161 indicates a range for calculating the appropriateness determination index 144. The operator is able to arbitrarily change the position, size and shape of the range through the input section 110. A table 162 is intended for inputting/displaying input parameters. As the input parameters, there are mentioned the number of standard materials and the type thereof. In the present GUI, there are selected two standard materials. A bone is selected for the standard material 1 (Material 1), and water is selected for the standard material 2 (Material 2), respectively. These standard materials are respectively displayed by bringing a cursor onto an input field of the standard material 1 or the standard material 2, for example and can be selected by clicking the standard material therein.

When the above-described input is done and a photography completion button (input completion button in the case of the data processing device) 166 when the X-ray CT device is used, for example is pressed, the calculation is carried out. When the appropriateness determination index 144 is created by the processes already described in each embodiment and its modification, the appropriateness determination index 144 is displayed as a graph 163, for example. There is shown herein the case where the same graph as that shown in FIG. 15(a) is displayed.

While viewing the appropriateness determination index 144, the operator inputs through a button 164 whether the standard material is appropriate (Good) or inappropriate (NG). When the inappropriateness (NG) is selected, the standard material can be selected again. When the button 166 for the photography completion or input completion is pressed again after the selection, a graph of the appropriateness determination index 144 is created. When the appropriateness (Good) is selected, a density image is created and displayed. This image is one example of the multi-energy image 145 created at the multi-energy image creating unit 53. An image 165-1 is an image for the standard material 1, and an image 165-2 is an image for the standard material 2.

Using such a GUI enables the photographer to select the appropriate standard material.

However, the GUI illustrated in FIG. 17 is one example and does not limit the present invention. For example, the screens illustrated in FIG. 8 are also made possible as a standard material input screen. The image, graph, input method and selection method shown in FIG. 17 may also assume various other forms. Also, there may be a case where some thereof are absent. Further, it is needless to say that it is possible that other information is added. Also, the method of displaying the standard material 1 or the standard material 2 and its selection method are also one example. There is shown in the GUI, a list of materials to be selectable, for example. The standard materials are selected from the list, and the kind and number thereof may be determined.

[Applications]

Although each embodiment and its modification described above have realized that the detection X-ray energy range is changed by changing the spectrum of each X-ray to be irradiated or the energy threshold value at the execution of the energy separation by the X-ray detector, the present invention is not limited to this, and other various methods may be adopted which change the energy range of each X-ray detected by the X-ray detector in each energy range.

Although each embodiment and its modification described above have been described by taking for example the X-ray CT device for medical purposes, the present invention is not limited to this. It is needless to say that the present invention is applicable to any CT device equipped with a photon counting type radiation detector which separates radiation incident to a detecting element for each energy range to count the number of photons. As one example thereof, there may be mentioned an X-ray CT device for non-destructive inspection, an X-ray cone beam CT device, or the like.

Further, the present invention is not limited to the above-described embodiments and can be implemented by modifying the same in various ways within the scope not departing from the gist of the present invention in an implementation stage thereof. Further, the above embodiments include various stages, and various inventions can be extracted by appropriate combinations of a plurality of components disclosed. For example, some of all components shown in the embodiments may be deleted.

As one example thereof, there may be mentioned various radiation imaging devices which do not perform an image reconstructing process without having the multi-energy image creating unit 53 and which create and display the multi-energy projected data 144 and an image calculated based on it. As one example thereof, there may be mentioned an X-ray image diagnostic device, an X-ray image photographing device, an X-ray fluoroscopic device, mammography, a digital subtraction device, a nuclear medicine check-up device, a radiotherapy apparatus, etc.

INDUSTRIAL APPLICABILITY

According to the present invention, there can be provided an X-ray CT device which is capable of, when multi-energy photography is performed by an energy separation type detector, and a subject is separated into a plurality of standard materials to create images, indicating an index of whether the standard material is appropriate, and determining an appropriate standard material with satisfactory accuracy. Further, there can be provided an X-ray CT data processing device which is capable of, when a subject is separated into a plurality of standard materials by using data obtained by multi-energy photography to create images, indicating an index of whether the standard material is appropriate, and determining an appropriate standard material with satisfactory accuracy.

REFERENCE SIGNS LIST

100 . . . X-ray source, 101 . . . gantry rotating section, 103 . . . bed top plate, 104 . . . X-ray detector, 105 . . . arithmetic section, 50 . . . main control unit, 51 . . . correction processing unit, 52 . . . standard material arithmetic unit, 53 . . . multi-energy image creating unit, 106 . . . display section, 107 . . . control section, 108 . . . signal acquisition section, 109 . . . storage section, 110 . . . input section, 111 . . . spectrum changing section, 123-125 . . . sampling time, 126-127 . . . energy threshold value, 140 . . . data for calculation, 141 . . . defective element position map, 142 . . . sensitivity/X-ray distribution data, 143 . . . projected data, 144 . . . appropriateness determination index, 145 . . . multi-energy image, 146 . . . reconstructed image, 153-154 . . . density value (calculation result), 155-156 . . . energy value, 400 . . . X-ray detecting element, 401 . . . detection layer, 402-403 . . . electrode, 405 . . . reading circuit, 511 . . . defective element correcting part, 512 . . . air correcting part, 551 . . . standard material data calculating part, 552 . . . standard material appropriateness determination index creating part (index creating part), 553 . . . density image calculating part, 554 . . . reconstructing part, 555 . . . standard material determining part, 556 . . . standard material changing part, 900 . . . X-ray CT data processing device, 911 . . . standard material data calculating part, 912 . . . standard material appropriateness determination index creating part.

The invention claimed is:

1. An X-ray CT data processing device which processes CT data respectively acquired in a plurality of detection energy ranges and separates the CT data into predetermined standard materials to create standard material data, comprising:
a standard material data calculating part which calculates energy-independent physical quantities for a plurality of standard materials respectively, as a plurality of the standard material data for the same standard material, by using different combinations of a plurality of the CT data acquired in the plurality of detection energy ranges; and
an appropriateness determination index creating part which creates an appropriateness determination index being an index for determining an appropriateness of the standard material, based on a plurality of the standard material data calculated by the standard material data calculating part, wherein the appropriateness determination index is a similarity of a plurality of the standard material data to the same standard material, and wherein the similarity of the plurality of standard material data is a probability distribution that the plurality of standard materials are the same, wherein the standard material data calculating part and the appropriateness determination index creating part comprise at least one central processing unit (CPU).

2. The X-ray CT data processing device according to claim 1, wherein the standard material data calculated by the standard material data calculating part include at least one of a density image of the standard material, projected data of the density image, a presence rate of the standard material, and projected data of the presence rate.

3. The X-ray CT data processing device according to claim 1, wherein the appropriateness determination index is a graph representing the standard material data.

4. The X-ray CT data processing device according to claim 3, wherein the graph has one axis being the kind of the standard material or a representative value of the detection energy range, and another axis being a value of the standard material data.

5. The X-ray CT data processing device according to claim 1, further including a standard material determining part which determines using the appropriateness determination index whether each of the standard materials to be separated is appropriate, wherein the standard material determining part comprises at least one CPU.

6. The X-ray CT data processing device according to claim 5, further including a standard material changing part which changes the separated standard material,
wherein the standard material determining part compares respective appropriateness determination indices at the standard materials to determine an appropriate standard material, wherein the standard material changing part comprises at least one CPU.

7. The X-ray CT data processing device according to claim 1, further including:
a display which displays each material as the standard material, and
a selection part comprising at least one CPU which selects the standard material creating the appropriateness determination index from said each material displayed by the display.

8. An X-ray CT device comprising:
an X-ray generator which irradiates X-rays;
an X-ray detector which measures the X-rays to obtain CT data;
a controller which controls the X-ray generator or/and the X-ray detector to obtain the CT data in three or more different detection energy ranges; and
an arithmetic part comprising at least one CPU which processes the CT data and separates the CT data into predetermined standard materials to create a reconstructed image,
wherein the arithmetic part is equipped with an X-ray CT data processing device according to claim 1, and a reconstructed image creating part comprising at least one CPU which creates the reconstructed image by using the standard material data obtained in the X-ray CT data processing device, and wherein the arithmetic part performs an arithmetic operation related to a standard material, wherein the arithmetic operation comprises an appropriateness determination of the standard material.

9. The X-ray CT device according to claim 8, wherein the X-ray detector is an energy separation type detector which obtains X-ray photon signals by separation into a plurality of different energy ranges, and
wherein the controller obtains the projected data in the respective energy ranges of the X-ray detector to thereby acquire CT data in a plurality of the detection energy ranges.

10. The X-ray CT device according to claim 8, wherein the X-ray generator is equipped with a spectrum changing part comprising at least one CPU which changes generated X-ray spectrums and thereby realizes a plurality of the detection energy ranges, and
wherein the controller changes the X-ray spectrums at the spectrum changing part and acquires projected data with the respective X-ray spectrums at the X-ray detector to thereby obtain CT data in a plurality of the detection energy ranges.

11. The X-ray CT device according to claim 8, wherein the X-ray generator is equipped with a spectrum changing part comprising at least one CPU which changes generated X-ray spectrums,
wherein the X-ray detector is an energy separation type detector which obtains X ray photon signals by separation into a plurality of different energy ranges, and
wherein the controller changes the X-ray spectrums at the spectrum changing part and obtains the projected data in the respective energy ranges of the X-ray detector at the respective X-ray spectrums to thereby acquire CT data in a plurality of the detection energy ranges.

* * * * *